(12) United States Patent
Golemis et al.

(10) Patent No.: US 8,685,658 B2
(45) Date of Patent: Apr. 1, 2014

(54) COMPOSITIONS AND METHODS FOR THE TREATMENT OF DISEASES ASSOCIATED WITH ABERRANT CILIA ASSEMBLY AND REGULATION

(75) Inventors: Erica A. Golemis, Oreland, PA (US); Elena N. Pugacheva, Morgantown, WV (US)

(73) Assignee: Fox Chase Cancer Center, Jenkintown, PA (US)

( * ) Notice: Subject to any disclaimer, the term of this patent is extended or adjusted under 35 U.S.C. 154(b) by 552 days.

(21) Appl. No.: 12/374,209

(22) PCT Filed: Jul. 17, 2007

(86) PCT No.: PCT/US2007/073722
§ 371 (c)(1),
(2), (4) Date: Apr. 2, 2009

(87) PCT Pub. No.: WO2008/011430
PCT Pub. Date: Jan. 24, 2008

(65) Prior Publication Data
US 2009/0306183 A1 Dec. 10, 2009

Related U.S. Application Data

(60) Provisional application No. 60/831,479, filed on Jul. 17, 2006, provisional application No. 60/925,272, filed on Apr. 19, 2007.

(51) Int. Cl.
*G01N 33/567* (2006.01)
*G01N 33/53* (2006.01)
*G01N 33/573* (2006.01)

(52) U.S. Cl.
USPC ............ 435/7.21; 435/7.3; 435/7.4; 435/7.8; 435/325

(58) Field of Classification Search
None
See application file for complete search history.

(56) References Cited

U.S. PATENT DOCUMENTS

2006/0178318 A1 * 8/2006 Anand et al. .................... 514/27

OTHER PUBLICATIONS

Praetorius et al (J. Membrane Biol. 191: 69-76, 2002).*
Pan et al (Dev. Cell 6: 445-451, 2004).*
Pan (J. Biol. Chem. 275(31): 24106-24114, 2000).*
Praetorius et al (Curr. Op. Neph. Hypertension 12:517-520, 2003).*
Cheetham et al (J. Biol. Chem. 277(45): 42419-42422, 2002).*
Schermer et al (EMBO 24(24): 4415-4424, 2005).*
Pan et al (Laboratory Investigation 85:452-463, 2005).*
Praetorius, H. A., et al. "Removal of the MDCK Cell Primary Cilium Abolishes Flow Sensing." Journal of Membrane Biology, 191: 69-76 (2002).

* cited by examiner

*Primary Examiner* — Richard Schnizer
(74) *Attorney, Agent, or Firm* — Kathleen D. Rigaut; Dann, Dorfman, Herrell & Skillman

(57) ABSTRACT

Compositions and methods are provided for identifying agents which have efficacy for the treatment of disorders related to aberrant cilial structure and function, including polycystic kidney disease.

8 Claims, 32 Drawing Sheets

F.  IMCD-3

G.  Caki-1

H.

A.

B.

A.

B.

C.

COMPOSITIONS AND METHODS FOR THE TREATMENT OF DISEASES ASSOCIATED WITH ABERRANT CILIA ASSEMBLY AND REGULATION The present application is §371 application of PCT/US2007/073722 filed 17 Jul. 2007 which claims priority to U.S. Provisional Application No. 60/831,479 filed 17 Jul. 2006, and U.S. Provisional Application No. 60/925,272 filed 19 Apr. 2007, the entire disclosure of each being incorporated by reference herein.

Pursuant to 35 U.S.C. §202(c), it is acknowledged that the U.S. Government has certain rights in the invention described, which was made in part with funds from the National Institutes of Health, Grant Numbers RO1 CA63366 and CA-06927.

FIELD OF THE INVENTION

The present invention relates to the fields of molecular biology and cilia-associated structural and cellular signal transduction. More specifically, the invention provides methods for identifying compounds which modulate cilia assembly and disassembly, thereby providing treatment for disorders associated with aberrant coordination of cilia function, including, for example, polycystic kidney disease, renal cysts, cancer, hypertension and infertility.

BACKGROUND OF THE INVENTION

Several publications and patent documents are cited throughout the specification in order to describe the state of the art to which this invention pertains. Each of these citations is incorporated by reference herein as though set forth in full.

In polycystic kidney disease (PKD), Bardet-Biedl Syndrome (BBS), and other disorders, mutations in cilia-associated structural or signaling proteins cause insensitivity to external mechanical and diffusible signaling cues, resulting in disorganized, hyperplastic cell growth (Benzing and Walz, 2006; Pan et al., 2005; Singla and Reiter, 2006). On the organismal level, ciliary defects produce renal cysts, infertility, respiratory disorders, situs inversus, and predisposition to obesity, diabetes, and hypertension. Notably, recent studies have shown that the Hedgehog, Wnt, PDGFαα, and other signaling cascades are coordinated at cilia (Cano et al., 2004; Huangfu and Anderson, 2005; Liu et al., 2005; Schneider et al., 2005; Simons et al., 2005; Tanaka et al., 2005). The frequent deregulation of these pathways during cell transformation, together with the common disappearance of cilia in transformed cells, raises the possibility that defective ciliary signaling may promote cancer.

Although an increasing number of proteins are being defined as ciliary structural components or cilia-associated signaling proteins, very little is currently known about the cellular machinery controlling the formation and resorption of cilia. It has long been known that cilia are regulated dynamically throughout the cell cycle. In many cells, resorption occurs at mitotic entry, and reappearance after progression into G1. However, resorption is not solely linked to mitotic entry, with some cells undergoing waves of resorption at different points in cell cycle: for example, Tucker et al. have noted ciliary resorption as cells emerge from quiescence, prior to S-phase (Quarmby and Parker, 2005; Rieder et al., 1979; Tucker et al., 1979). Given their increasingly apparent role in detecting and transmitting extracellular signals, regulated formation, disassembly, or shortening of cilia may play an important role in cellular growth controls, serving as a rheostat to limit response to overly persistent or abnormal cell growth cues in the extracellular environment.

A cilium arises from a basal body, a structure that differentiates from one of the centrioles in the centrosome in non-proliferating cells and organizes the microtubule bundles that constitute the ciliary axoneme. Cilia are evolutionarily related to the motile flagella of lower eukaryotes, such as the green algae *Chlamydomonas*. Genetic studies in *Chlamydomonas* have recently begun to dissect the process of flagellar resorption (Bradley and Quarmby, 2005; Marshall et al., 2005; Pan and Snell, 2005; Quarmby, 2004). These studies have identified altered functionality of the intraflagellar transport (IFT) machinery and destabilization of the axoneme as hallmarks of disassembly, and implicated CALK and other kinases as regulators of disassembly. The means by which CALK becomes activated at initiation of disassembly and the critical CALK, effectors in the disassembly process remain unknown, as does the relevance of these observations to higher eukaryotes.

CALK is very distantly related to the human Aurora A (AurA) kinase, with 55% similarity centered on the protein catalytic domain. In humans, Aurora A (AurA) is a centrosomal kinase that regulates mitotic entry through activation of Cdk1-cyclin B and other substrates that organize the mitotic spindle (Bischoff et al., 1998; Marumoto et al., 2005). AurA amplification or activation is common in many cancers characterized by centrosomal amplification and genomic instability (Anand et al., 2003; Goepfert et al., 2002; Gritsko et al., 2003). In the past year, altered expression of the HEF1 (Law et al., 1996; O'Neill et al., 2000) scaffolding protein has recently been identified as part of a pro-metastatic signature in breast cancer (Minn et al., 2005), shown to contribute to the aggressiveness of glioblastomas (Natarajan et al., 2006), and found to be critical for progression to metastasis in melanomas (Kim et al., 2006). HEF1 is best known as a transducer of integrin-initiated attachment, migration, and anti-apoptotic signals at focal adhesions (O'Neill et al., 2000).

SUMMARY OF THE INVENTION

In accordance with the present invention, methods for identifying agents which modulate ciliary function and assembly/disassembly are provided. An exemplary method entails providing cells which express AurA and HEF1 and incubating the cells in the presence and absence of the agent. Following treatment, the cilia present on the cells are assessed for alterations which occur in the presence but not the absence of the agent, agents which cause alterations being identified as modulators of ciliary function and assembly.

In yet another aspect of the invention, an in vivo model for assessing agents which modulate kidney cyst formation is provided. In the model, a first strain of mice in which Pkd1 is conditionally inactivated is provided and the mice crossed with each of the following mice, i) a transgenic HEF-1 knock out mouse; ii) a mouse expressing functional HEF-1 and iii) a third strain of mice which are heterozygous for HEF-1 expression. After crossing, Pkd1 is inactivated and a test agent administered to each of the newly created strains of mice. After a suitable time period of administration, the mice are assessed to determine whether the agent modulates cyst formation relative to untreated mice.

A. Assembly of cilia. An average of 200 cells were counted in two independent experiments B. Disassembly of cilia induced by serum stimulation. An average of 150 cells were counted in each of 4 experiments. C. Immunofluorescence of quiescent cells with antibody to AurA (green), acetylated α-tubulin (blue), and DNA (red). Scale bar 10 µm. In this and subsequent panels, boxes in main image indicate structures shown at high magnification to right. D. Immunofluorescence of quiescent cells with polyclonal rabbit antibody to HEF1 (green), also visualizing acetylated α-tubulin (blue), and DNA (red); compare also to E. Scale bar 10 µm, E. Immunofluorescence of quiescent cells with monoclonal antibody to HEF1 (green), also visualizing γ-tubulin (blue) and DNA (red). Scale bar 5 µm. See also FIG. 6A. F. Immunofluorescence of quiescent cells with antibody to phospho-AurA (green), acetylated α-tubulin (blue), and DNA (red). Scale bar 12.5 µm. G. Immunofluorescence of serum-stimulated cells with antibody to phospho-AurA (green), acetylated α-tubulin (blue), and DNA (red). Scale bar 5 µm. H. Western analysis of AurA and HEF1 in hTERT-RPE1 cells after serum stimulation. Western blots shown represent strips and reprobes of a single gel. Higher molecular weight HEF1 band reflects hyperphosphorylation, and coincides with AurA activation and ciliary disassembly at 2 and 24 hours after serum addition (at time point 0). Light gray arrow indicates crossreactivity of phospho-AurA directed antibody with total AurA; black arrow indicates phospho-AurA. See also FIG. 2H. I. Immunofluorescence depicting AurA activation in serum-stimulated cells during disassembly of cilia. All images are merged panels of acetylated α-tubulin (red), phospho-AurA or total AurA (green) and DNA (blue).

Figure 2:
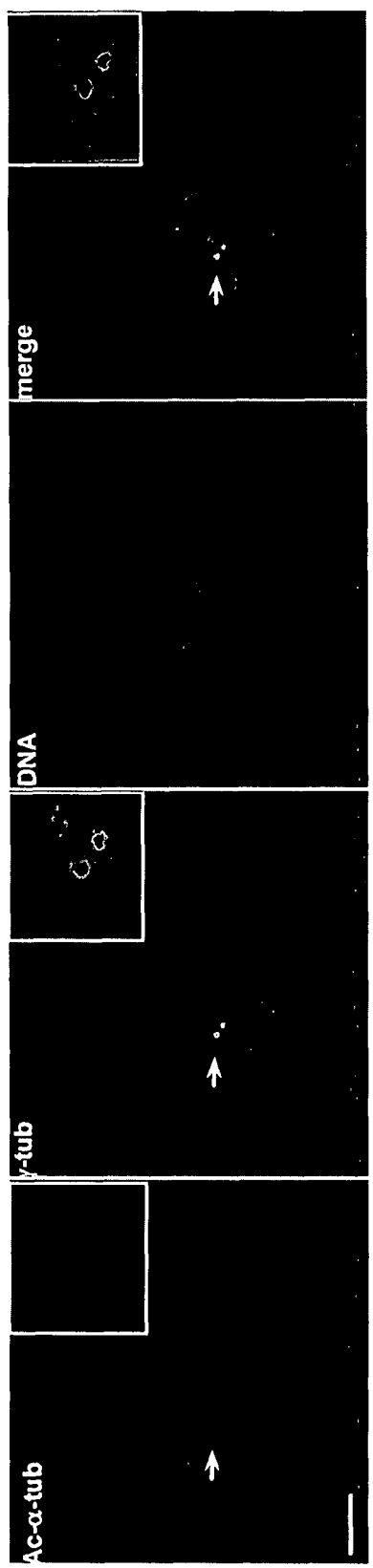
Figure 2:
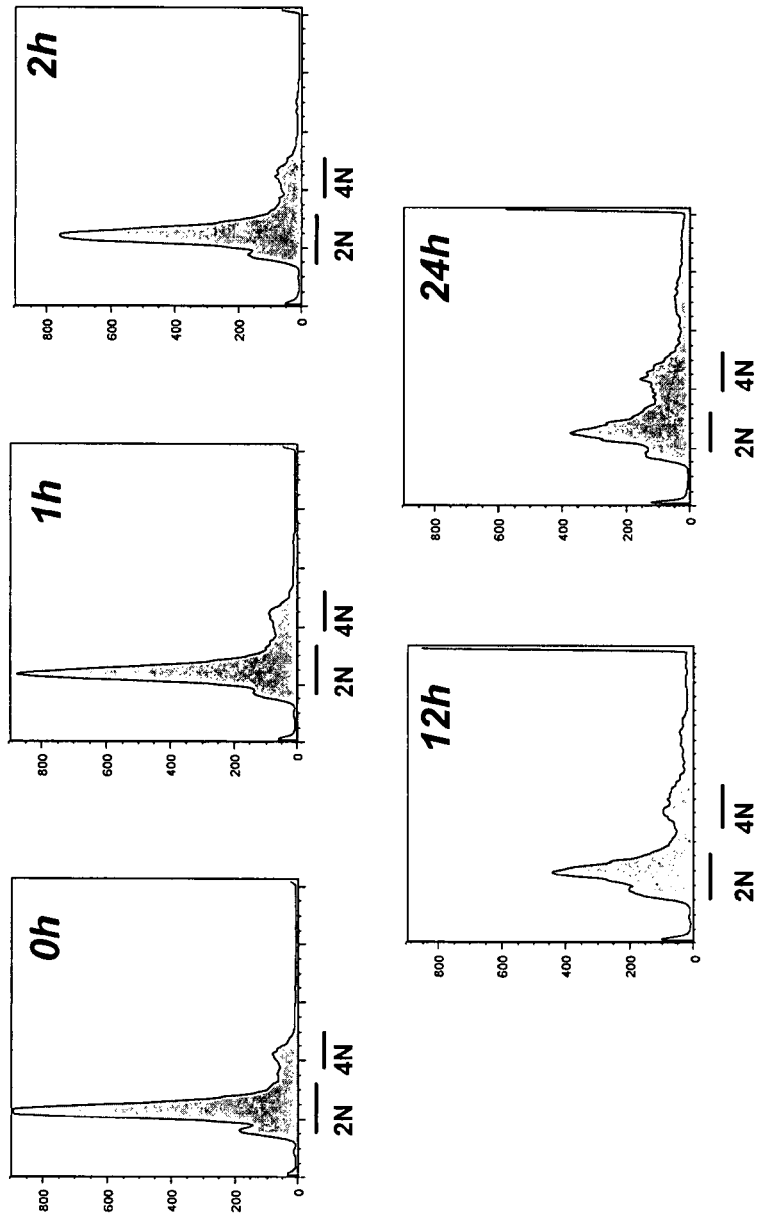
Figure 2:
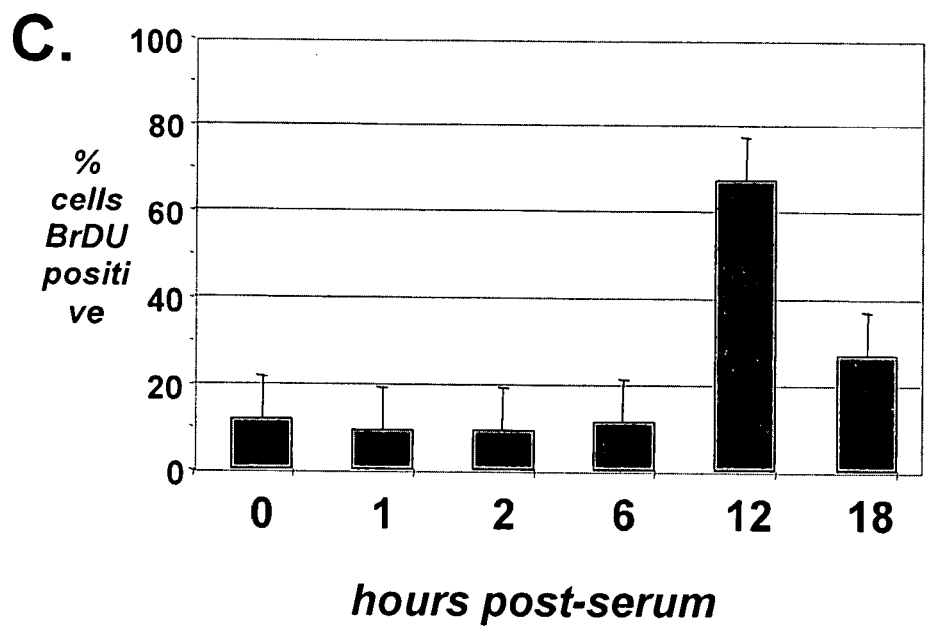
Figure 2:
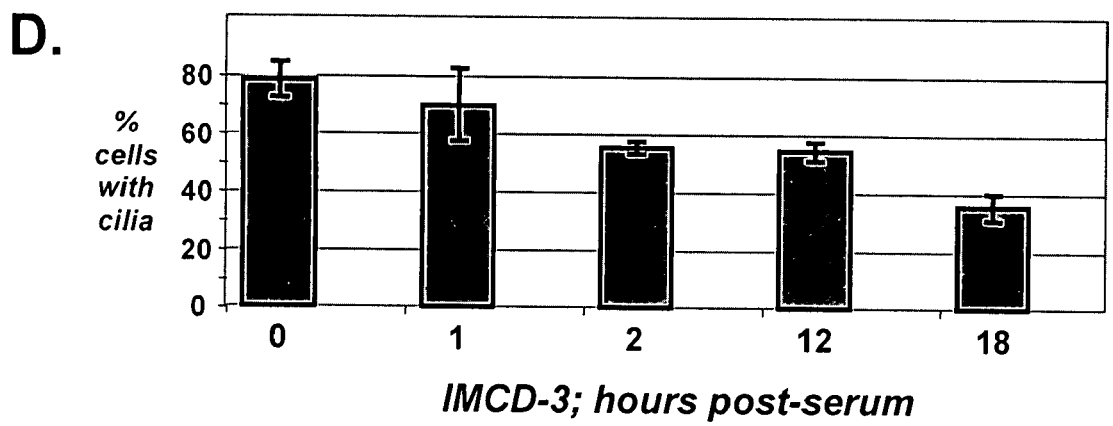
Figure 2:
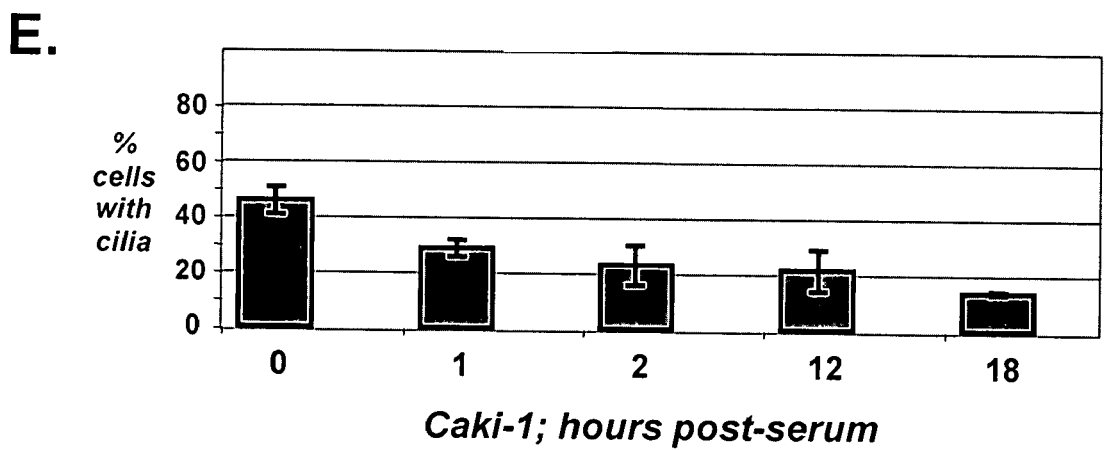
Figure 2:
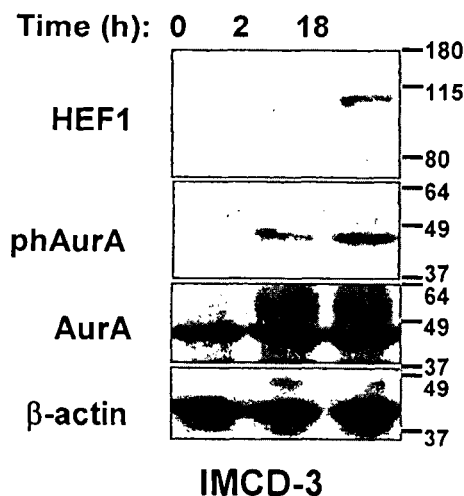
Figure 2:
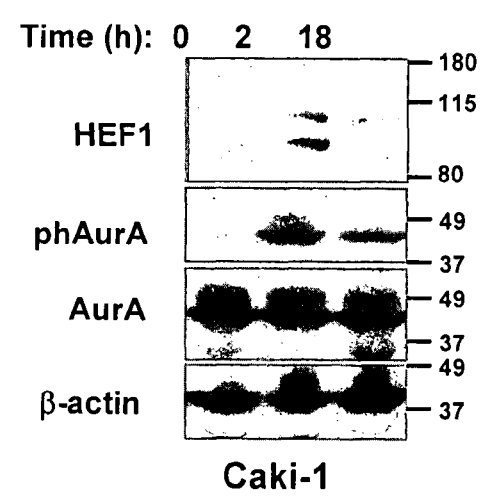
Figure 2:
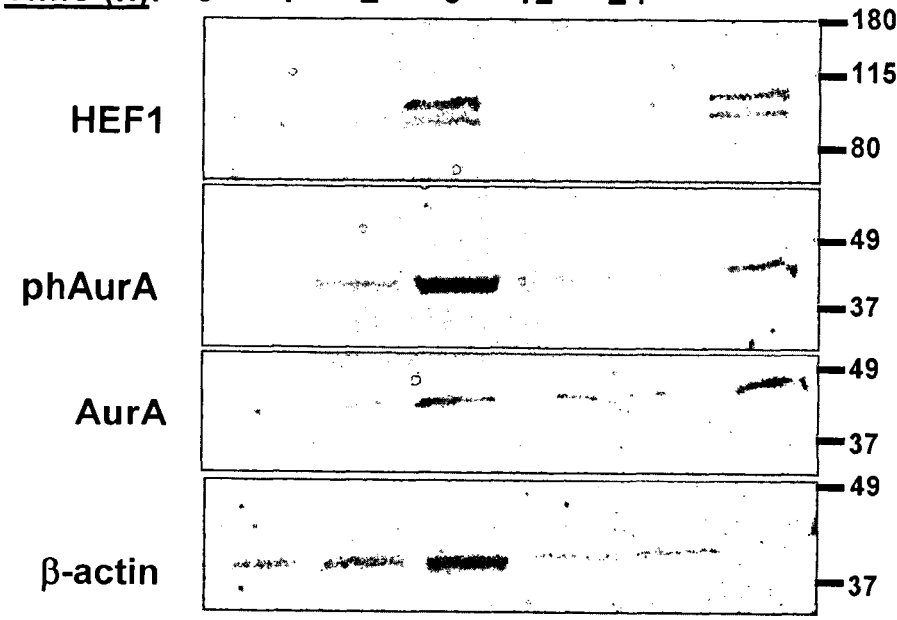
Figure 2:
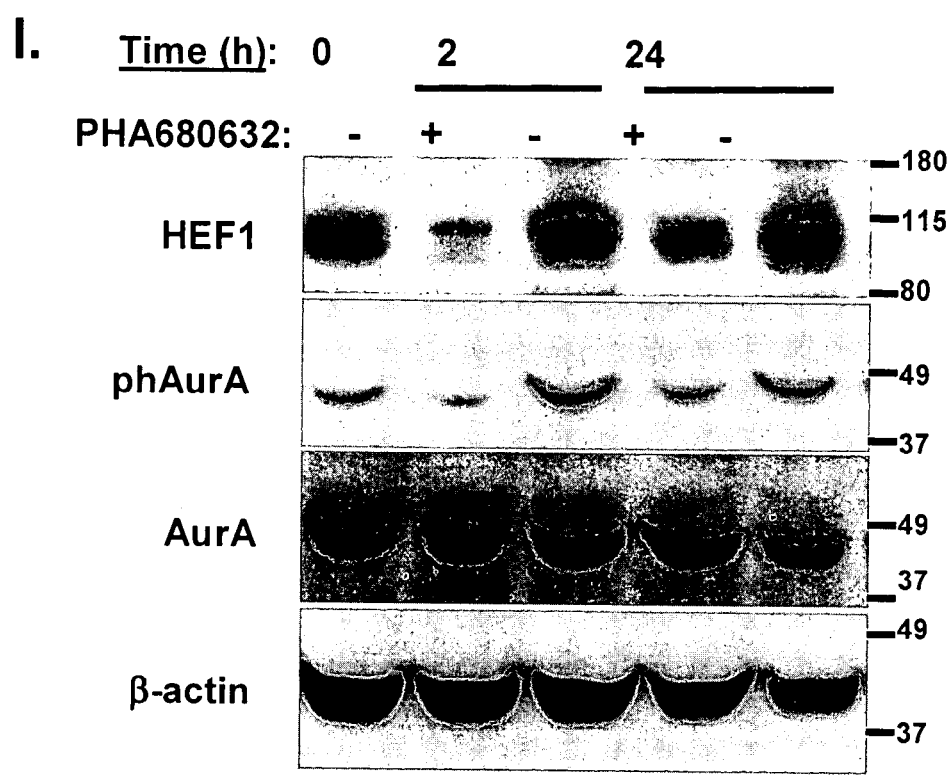

FIG. 2. Profile of Serum Induced Disassembly of Cilia in hTERT-RPE1, IMCD3, and Caki-1 Cells.

Figure 3:
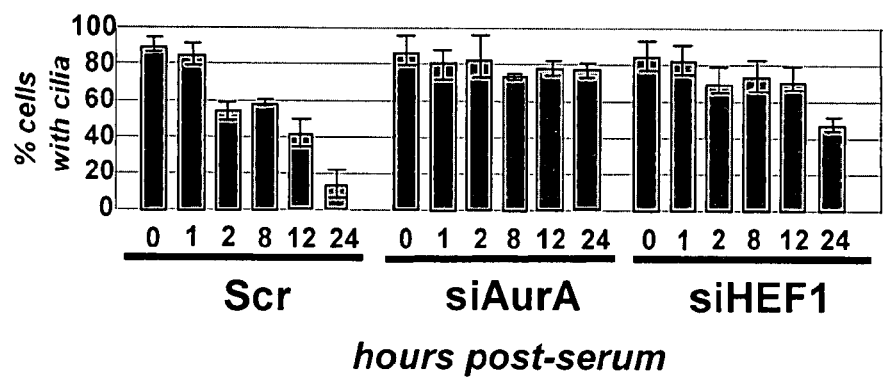
Figure 3:
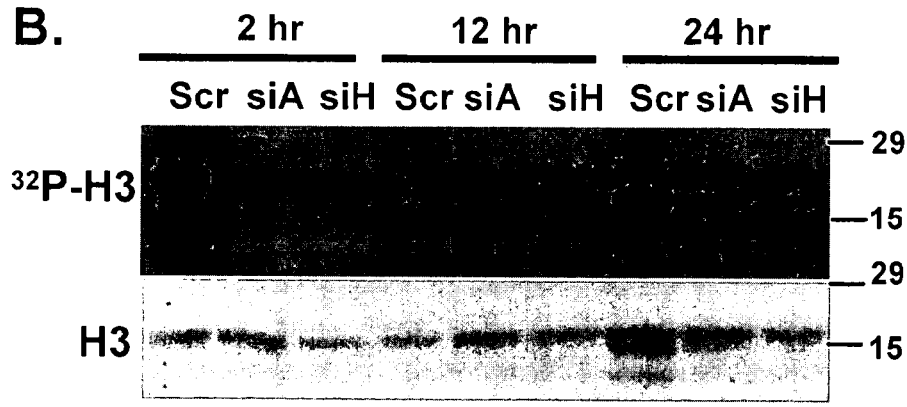
Figure 3:
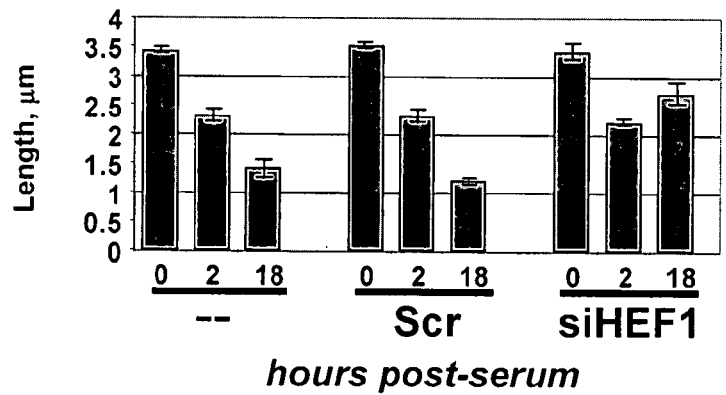
Figure 3:
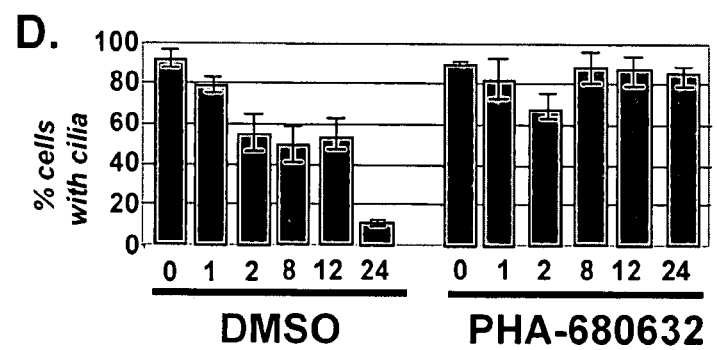
Figure 3:
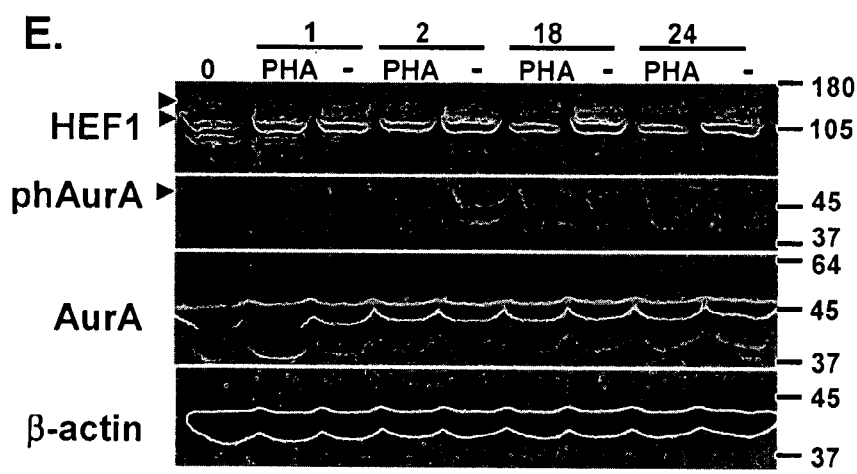
Figure 3:
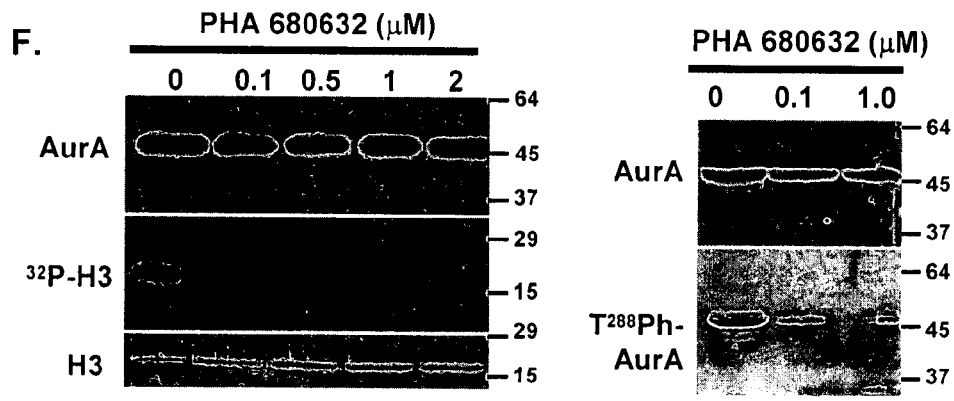
Figure 3:
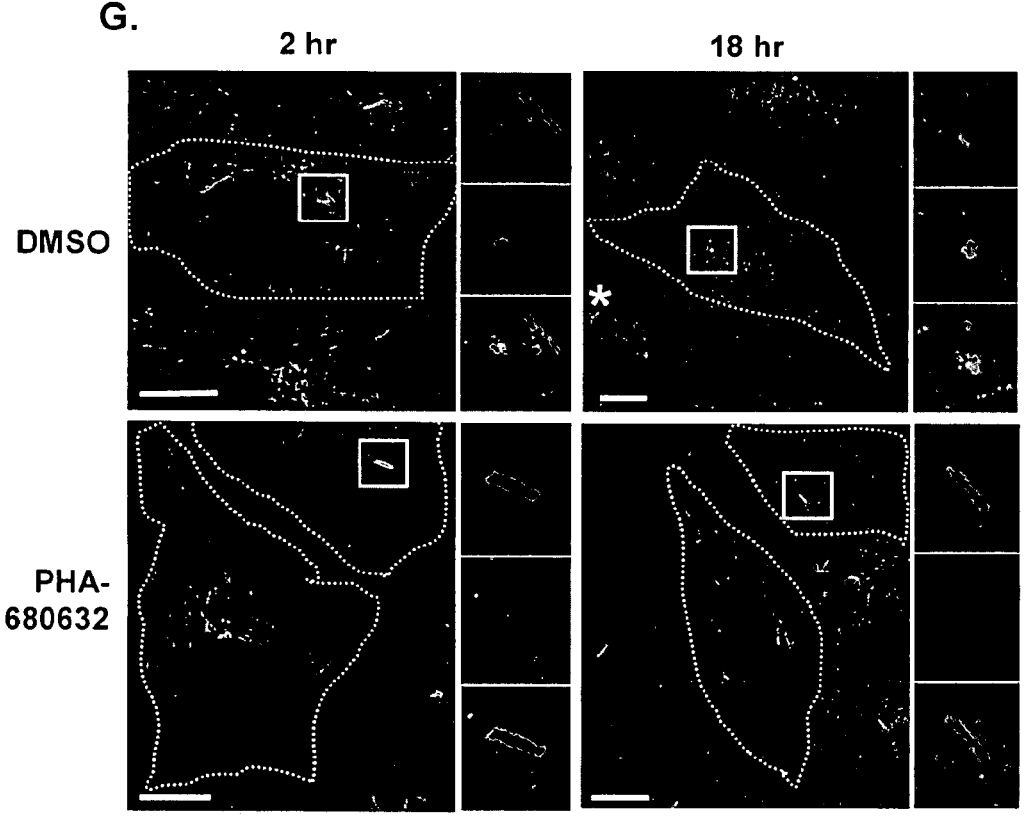
Figure 3:
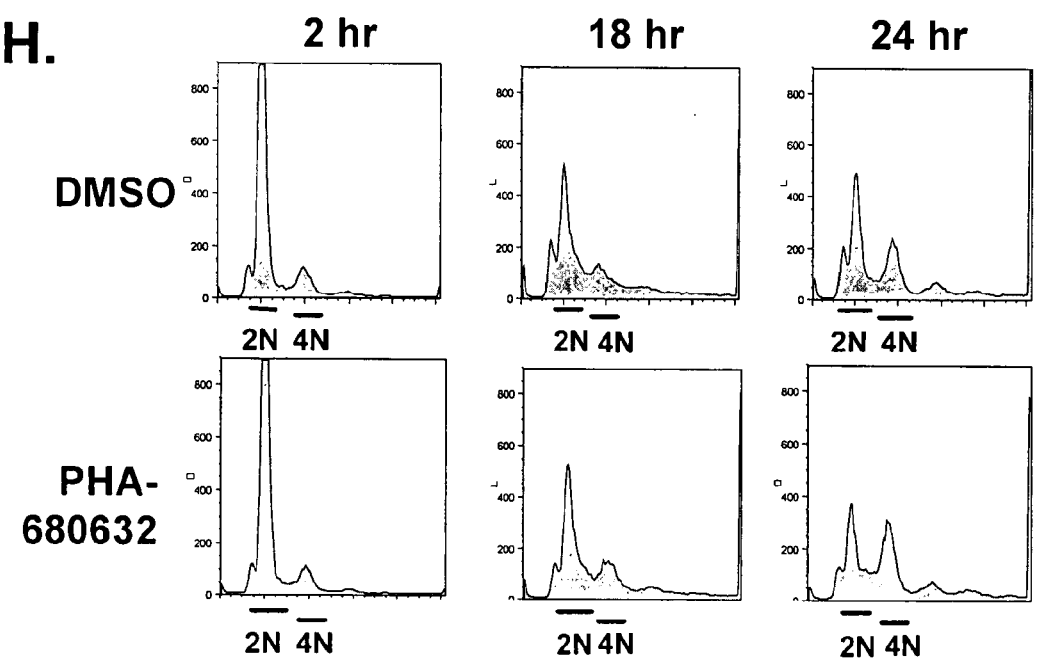

A. Immunofluorescence analysis of cilia in quiescent hTERT-RPE1 cells. Cilia are visualized with antibodies to acetylated α-tubulin (Ac-α-tub, blue). The basal body and the second cellular centriole are visualized with antibodies to γ-tubulin (γ-tub, green), while DNA is indicated in red (PI), Insets are enlarged view of structures marked with arrowhead. Scale bar 10 µm. Note, some later analyses (FIGS. 8, 10) use glutamylated α-tubulin as a second marker for cilia. B. FACS profile of cells at hours (h) indicated after serum treatment of quiescent hTERT-RPE1 cells. Approximate 2N and 4N peaks are marked; cells at 24 hours show marked reduction of G1, and increased G2/M compartmentation. Cells>4N reflect aggregated cells, as well as a very small population that have failed cytokinesis. C. Quantification of BrDU-staining in cells confirms the peak of S-phase occurs at ~12 hours after treatment of cells with serum. D., E. Time course of disassembly of cilia induced by serum stimulation in IMCD3 (D) and Caki-1 (E) cell lines. F., G. Western blot with antibodies to HEF1, AurA, and T288-phospho-AurA (phAurA) at 0, 2, and 18 hours after serum stimulation (see D, E) in IMCD-3 (F) and Caki-1 (G) cells. H. Experiment as in FIG. 1H, except using Cell Signaling antibody to visualize phospho-AurA. I. Experiment as in FIG. 3E, except using Cell Signaling antibody to visualize phospho-AurA FIG. 3. Activation of AurA is Necessary for Ciliary Resorption.

A. Disassembly of cilia in cells treated with siRNA to AurA or HEF1, or with Scrambled (Scr) control siRNA, for 0 to 24 hours after serum addition. Assay performed 3 times, with an average of 100 cells counted/experiment by acetylated tubulin staining. Results were confirmed using a second antibody (anti-glutamylated tubulin) to independently score cilia following depletion (FIGS. 8D, 10E). B. Ciliary disassembly was induced in ciliated cells pre-treated with control (Scr), AurA-targeted (siA), or HEF1-targeted (siH) siRNA by supplementing growth media with serum. At 2, 12, and 24 hours after addition of serum, AurA was immunoprecipitated and used for an in vitro kinase assay as in (Pugacheva and Golemis, 2005). Shown, $^{32}$P-labelled phosphorylated histone H3 (top) and total histone H3 in the reaction (stained with Coomassie Blue, bottom). C. Length of cilia in untreated hTERT-RPE1 cells (--), or the hTERT-RPE1 cells treated with control (Scr) or HEF1 targeting siRNA, at the indicated time points, D. Ciliated hTERT-RPE1 cells were treated with AurA inhibitor (PHA-680632) or DMSO, then disassembly of cilia tracked for 24 hours post serum addition. The in vitro IC50 of PHA-680632 is 27 nM for AurA; this compound also less potently inhibits AurC, AurB, and FGFR1 (IC50 120, 185, and 390 nM, respectively, (Soncini et al., 2006)). Results were confirmed using anti-glutamylated tubulin, as shown in FIG. 8D. E. Analysis performed in parallel with experiments described in D demonstrates PHA-680632 blocks appearance of $T^{288}$-phospho-AurA (visualized with antibody from BioLegend), and HEF1 phosphorylation (115 kDa form), in reference to DMSO (-) at the 2 and 24 hour time points. Black arrows marks phosphorylated AurA, and hyperphosphorylated (p115) HEF1; gray arrow indicates p105 HEF1. See also FIG. 2I. F. Cells were treated with indicated concentrations of the AurA inhibitor PHA-680632, and then AurA immunoprecipitated, and used for in vitro kinase reactions (left) or whole cell lysates used for Western analysis with antibody to total or phosphorylated AurA (right). G. Immunofluorescence analysis of appearance of phospho-AurA at times indicated after serum stimulation in DMSO- or PHA-680632-treated cells. DNA (blue), acetylated α-tubulin (red), and $T^{288}$-phospho-AurA (green). In 18 hr DMSO/ph-AurA, an asterisk (*) marks a rare observation of phospho-AurA at the base of a shortened cilium. H. FACS analysis of cells treated with DMSO vehicle or PHA-680632 at the times indicated after serum stimulation.

Figure 4:
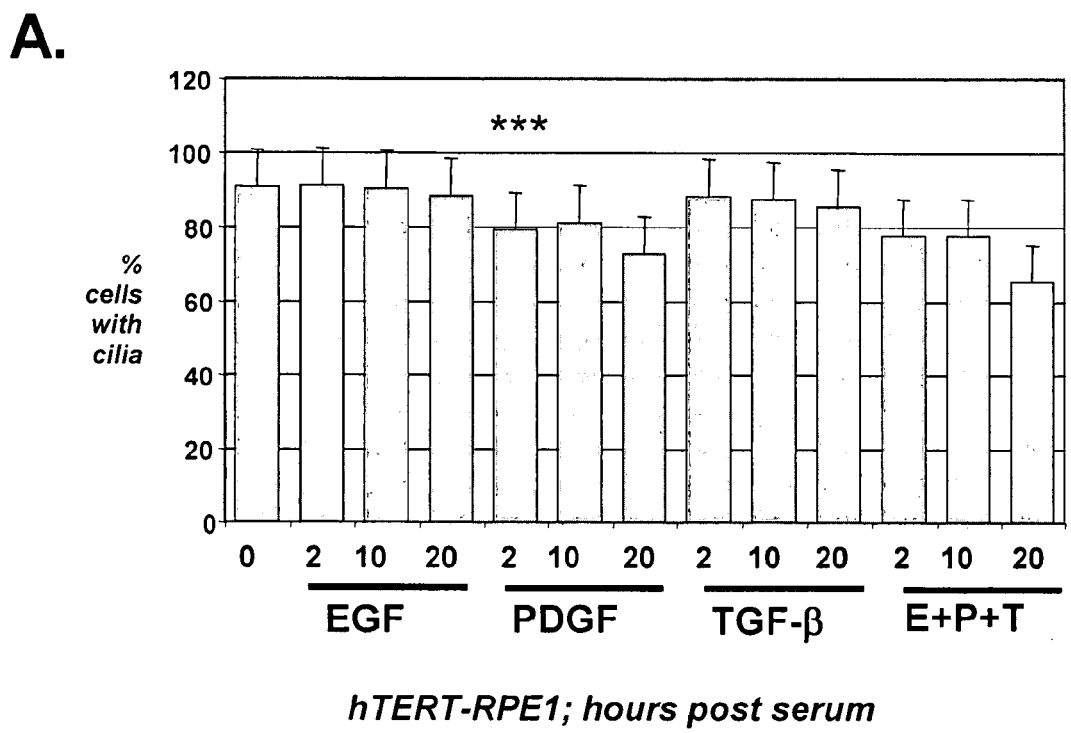
Figure 4:
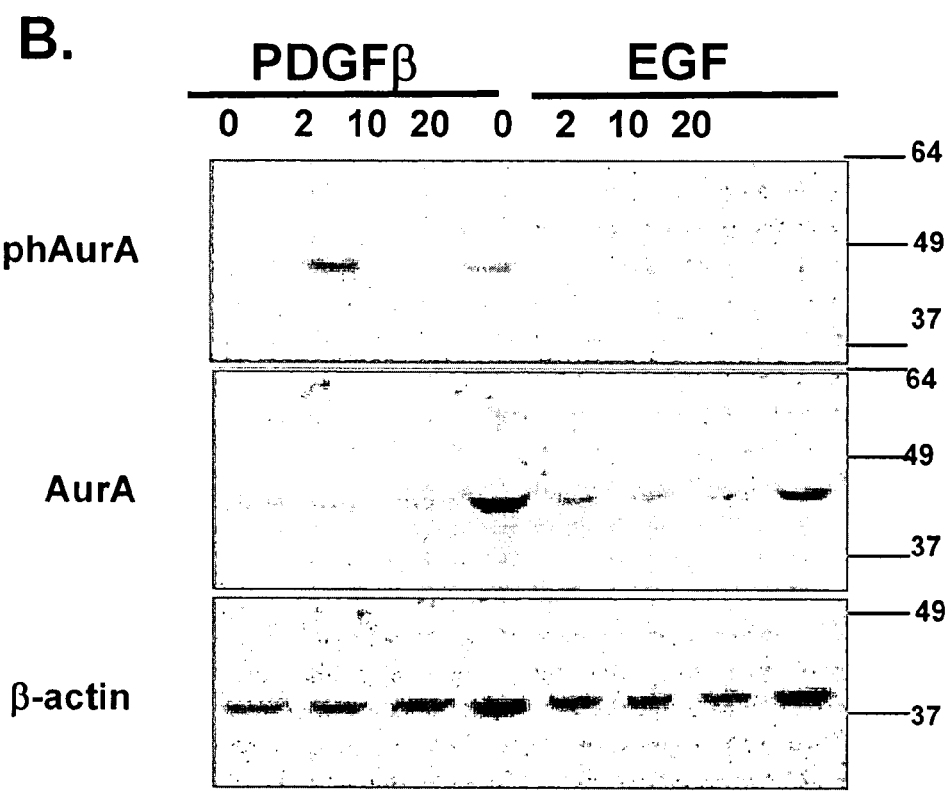
Figure 4:
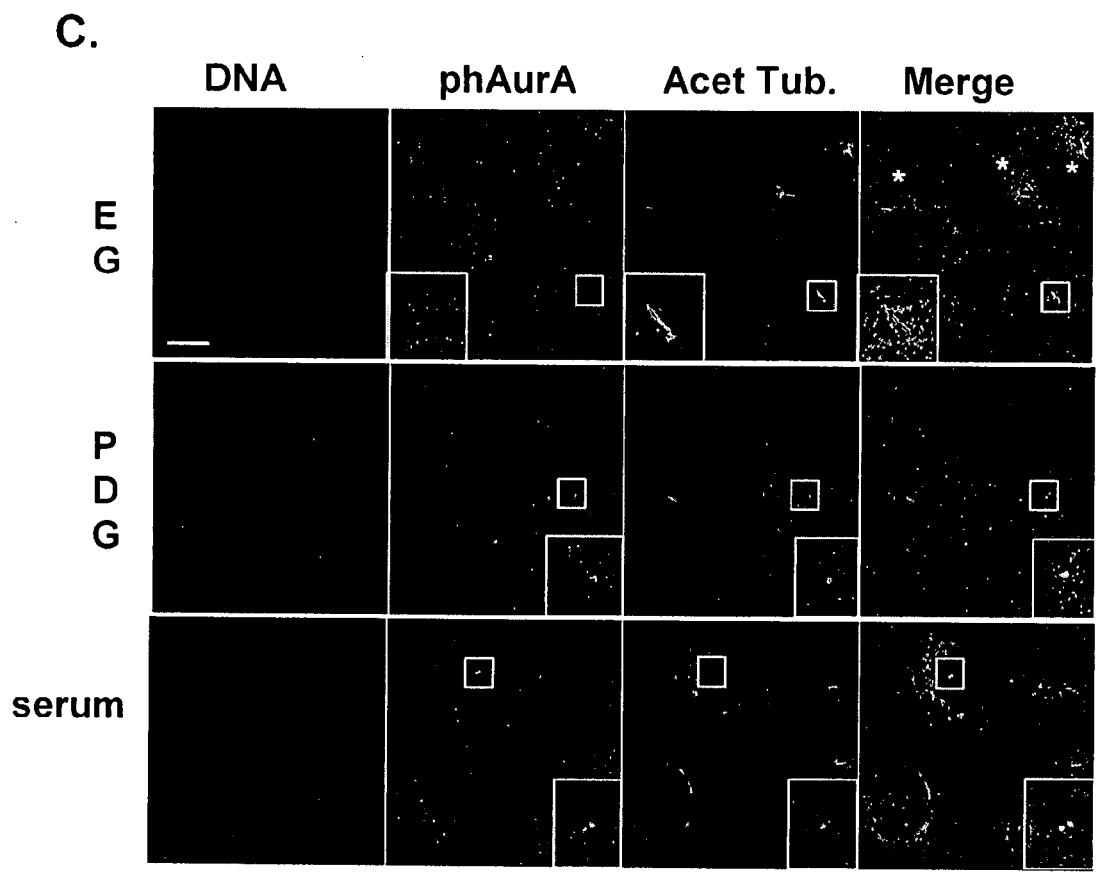

FIG. 4. Growth factor-induced disassembly of cilia in hTERT-RPE1 cells. A. Time course of disassembly of cilia in cells treated with EGF, PDGF, and TGF-β. To induce disassembly, hTERT-RPE1 cells were treated with EGF (10 ng/ml, Sigma), PDGF (10 ng/ml Sigma), and TGF-β (10 ng/ml, R&D Systems), and otherwise assayed as for serum treated cells. ***, one-way ANOVA indicates that reduction of cilia induced by PDGF is statistically significant (p<0.001) by 2 hours after treatment of cells. B. Western blot indicating T288-phosphorylated and total AurA in cells treated with PDGF or EGF, at times indicated after treatment. C. Immunofluorescence depicting cilia (red, acetylated a α-tubulin) and phospho-AurA (green) staining at the basal body at 2 hours after stimulation with PDGF, EGF, or serum. Phosphorylated AurA is apparent in PDGF- and serum-treated cells, but not EGF-treated cells: further, many well-formed cilia are apparent in EGF-treated cells (marked with asterisks) in contrast to other conditions. Scale bar represents 10 µM.

Figure 5:
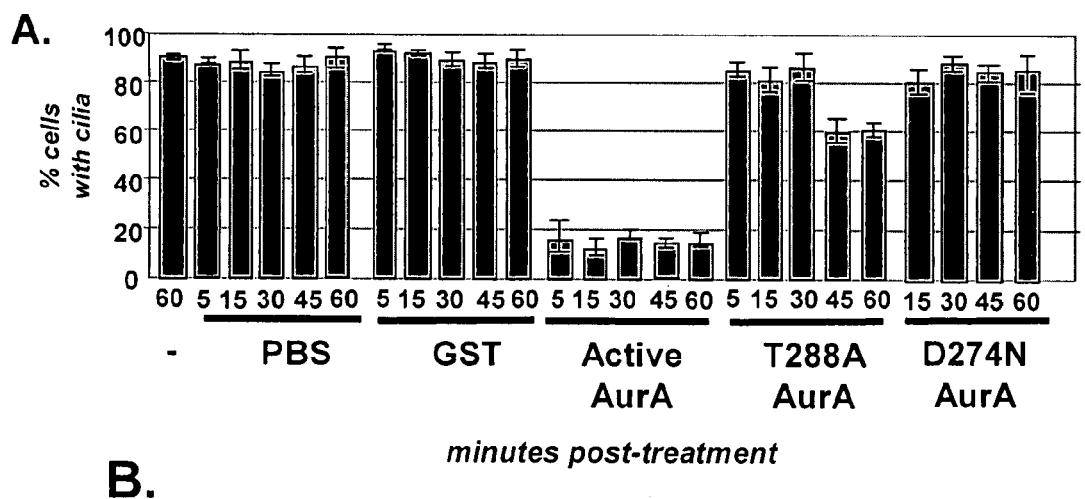
Figure 5:
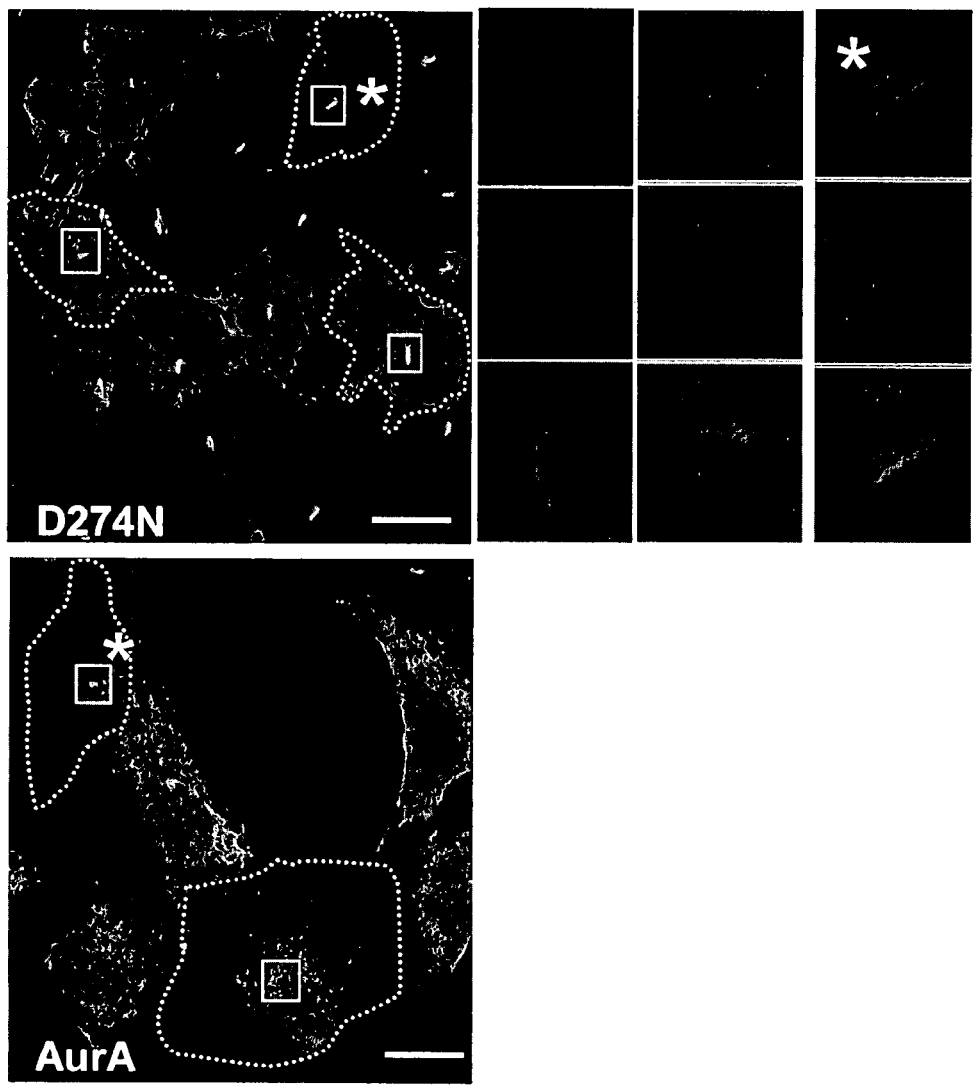
Figure 5:
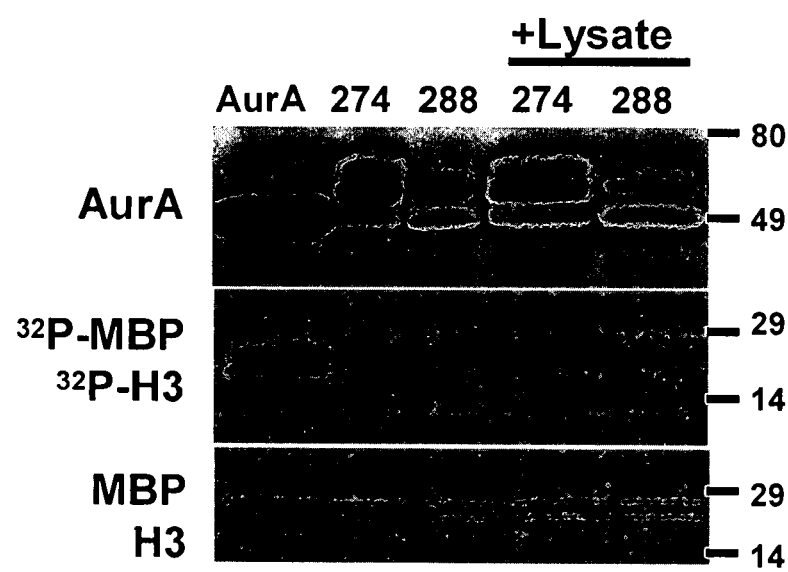

FIG. 5. Microinjection of Active AurA Causes Rapid Loss of Cilia.

A. Microinjection of wild type AurA, T288A or D274N mutant AurA, or GST, or PBS buffer, into hTERT-RPE1 cells with pre-formed cilia. (-), uninjected controls. Time reflects minutes from injection to initiating fixation of slides. Experiments repeated 3 times, with >100 injected cells scored in each experiment, B. Cilia 45 minutes post-injection of AurA or D274N. Red, acetylated α-tubulin; blue, glutamylated α-tubulin (a second independent marker of cilia); blue, DNA; green, Dextran488 indicates injected cells. High magnification images to right are from boxed cells; * marks magnification of uninjected cells. C. AurA and mutants (D274N, T288A) were incubated with histone H3 (17 kD) and MBP (22 kD) substrates in an in vitro kinase assay, confirming the activity of kinase, +Lysate indicates that mutants were incubated for 3 hours at 4° C. with hTERT-RPE1 cell lysate, then pulled down and used for the kinase assay.

Figure 6:
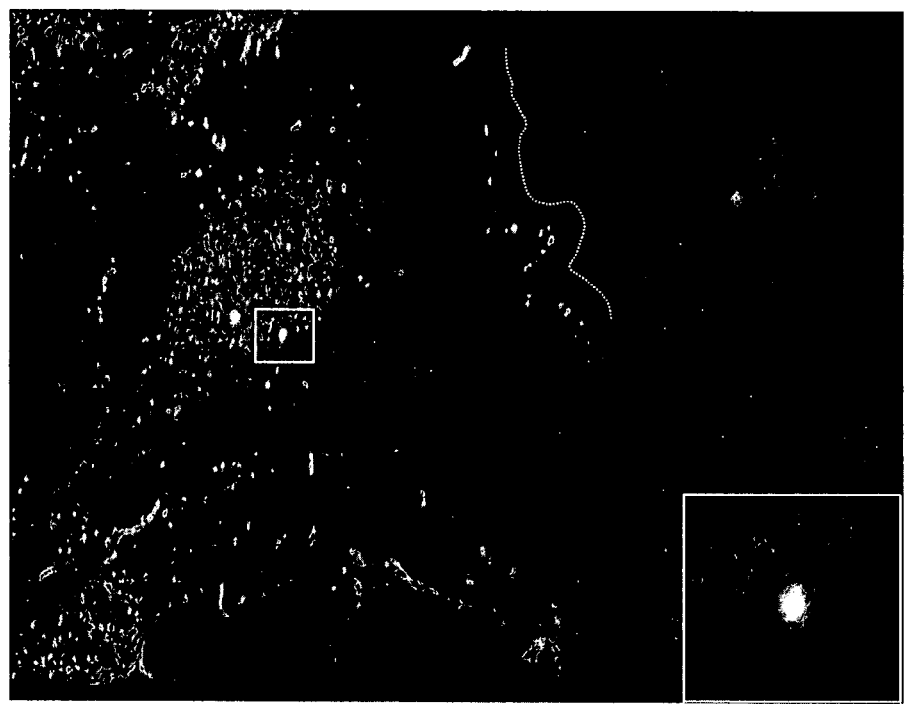
Figure 6:
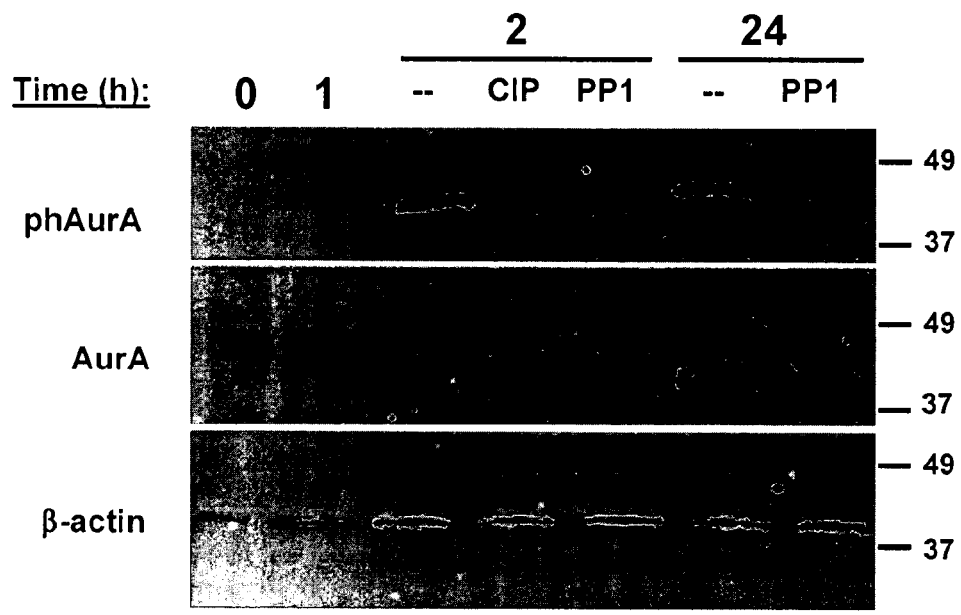

FIG. 6. A. Besides the Novel Localization of HEF1 at Cilia Described in Detail, HEF1 Also Localizes to Focal Adhesions in hTERT-RPE1 Cells, as Previously Reported for Many Other Cell Lines.

Shown, immunofluorescence of hTERT-RPE1 cells stained with antibody to HEF1 (green) and to acetylated α-tubulin (red) at 2 hours post-serum stimulation. Dotted line indicates HEF1 at focal adhesions; inset box shows basal body/centrosome. B. To confirm specificity of serum-induced phospho-AurA signal, antibody to T288-phospho-AurA (Cell Signaling) and total AurA was used to probe Western blots of untreated or phosphatase-treated hTERT-RPE1 cells at the times indicated after serum addition. CIP, calf intestinal phosphatase; PP1, protein phosphatase 1 (New England Biolabs) according to the manufacturer's recommendations.

Figure 7:
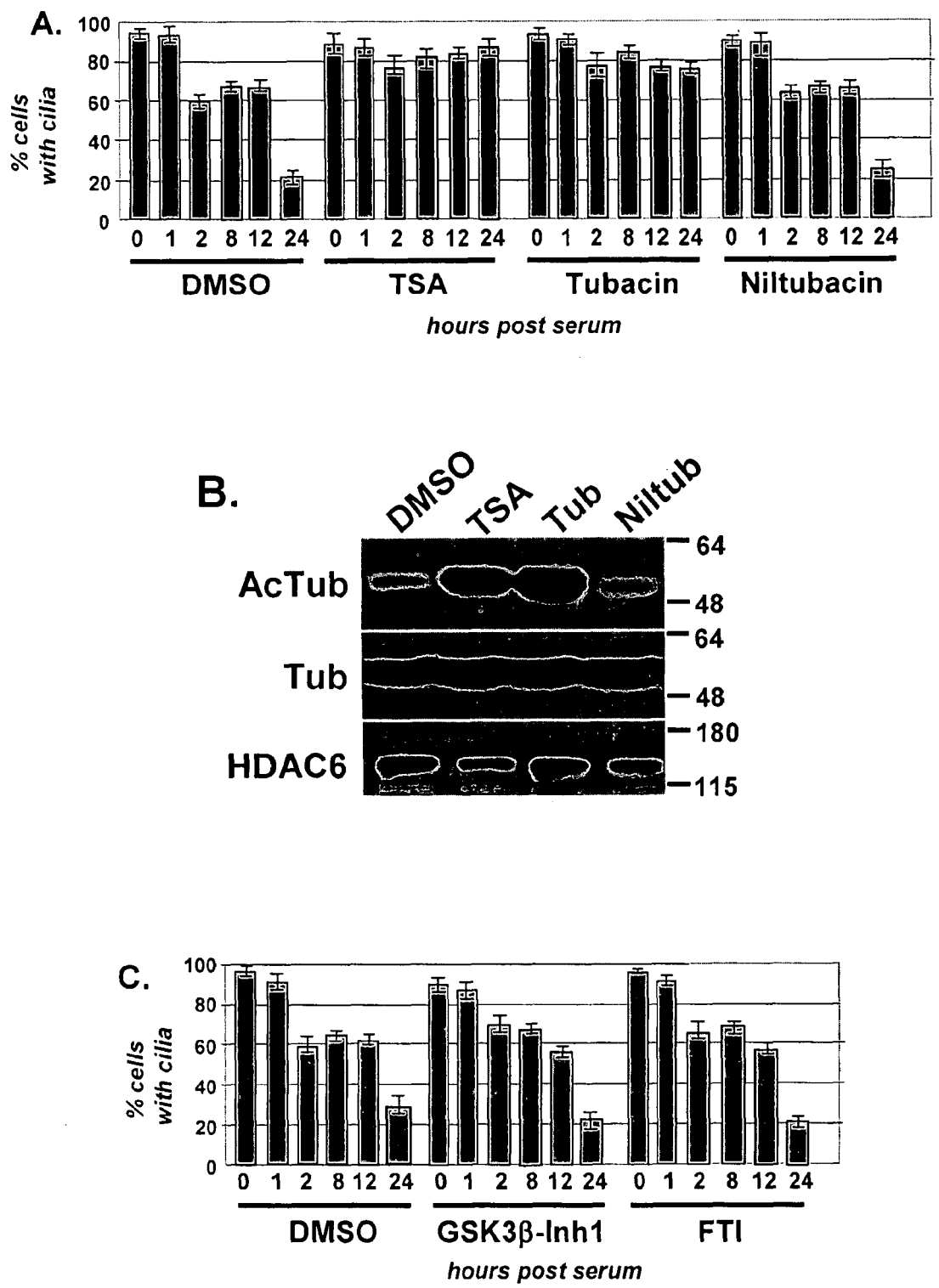
Figure 7:
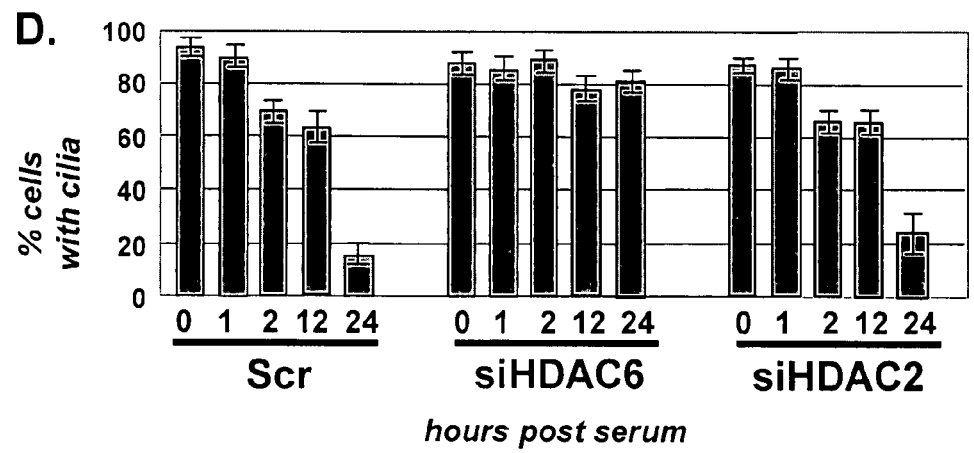
Figure 7:
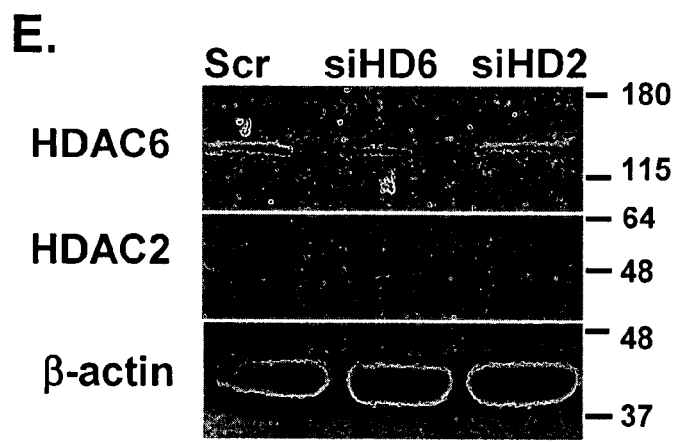
Figure 7:
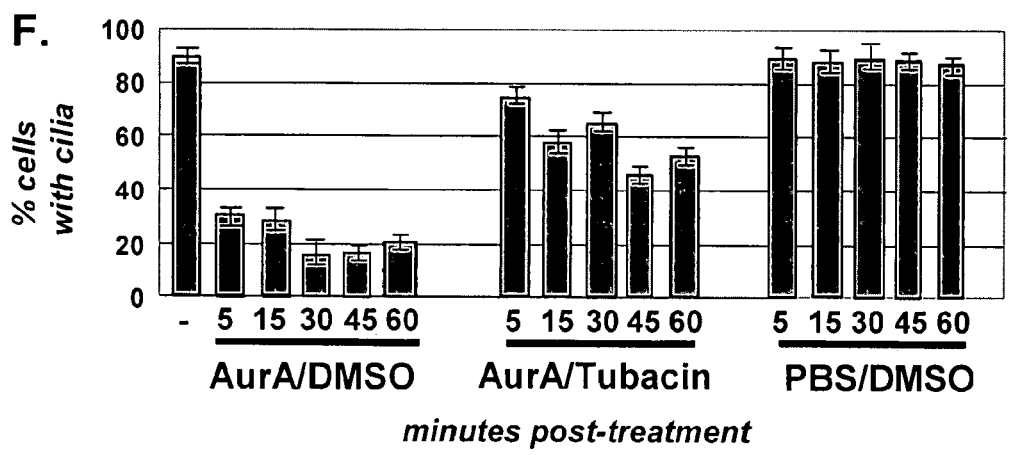

FIG. 7, HDAC6 Activity is Necessary for Resorption of Cilia.

A. Treatment of hTERT-RPE1 cells with histone deacetylase inhibitors prevents ciliary resorption. Cells were incubated with indicated compounds or vehicle (DMSO) at concentrations described in hereinbelow for 2 hours prior to induction of ciliary disassembly. The assay was performed 3 times, with an average of 100 cells counted/time point. B. TSA and tubacin increase intracellular levels of acetylated tubulin. Shown, Western blot with indicated antibodies showing levels of acetylated tubulin in cells treated with TSA, tubacin, nil tubacin, or vehicle (DMSO) C. GSK3β inhibitor and farnesyltransferase inhibitor (FTI) do not inhibit ciliary disassembly. D. Depletion of HDAC6 restricts serum-induced disassembly of cilia in hTERT-RPE1 cells transfected for 48 hrs with siRNAs to HDAC6, HDAC2, or a scrambled control. E. Western analysis of hTERT-RPE1 cells treated with siRNA to HDAC6, HDAC2, or scrambled control. F. Active AurA or PBS were microinjected into hTERT-RPE1 cells pretreated for 2 hours with tubacin or DMSO.

Figure 8:
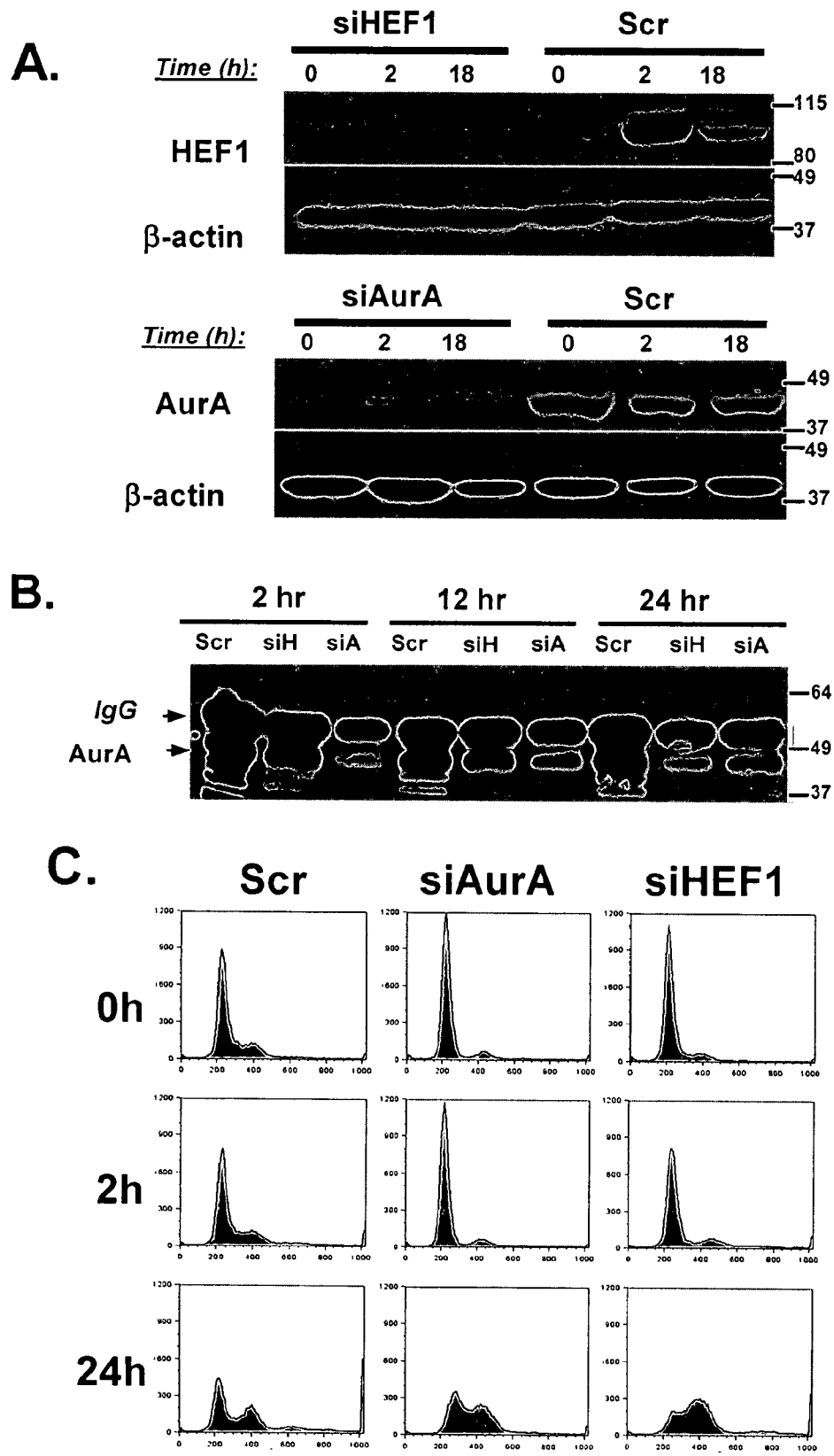
Figure 8:
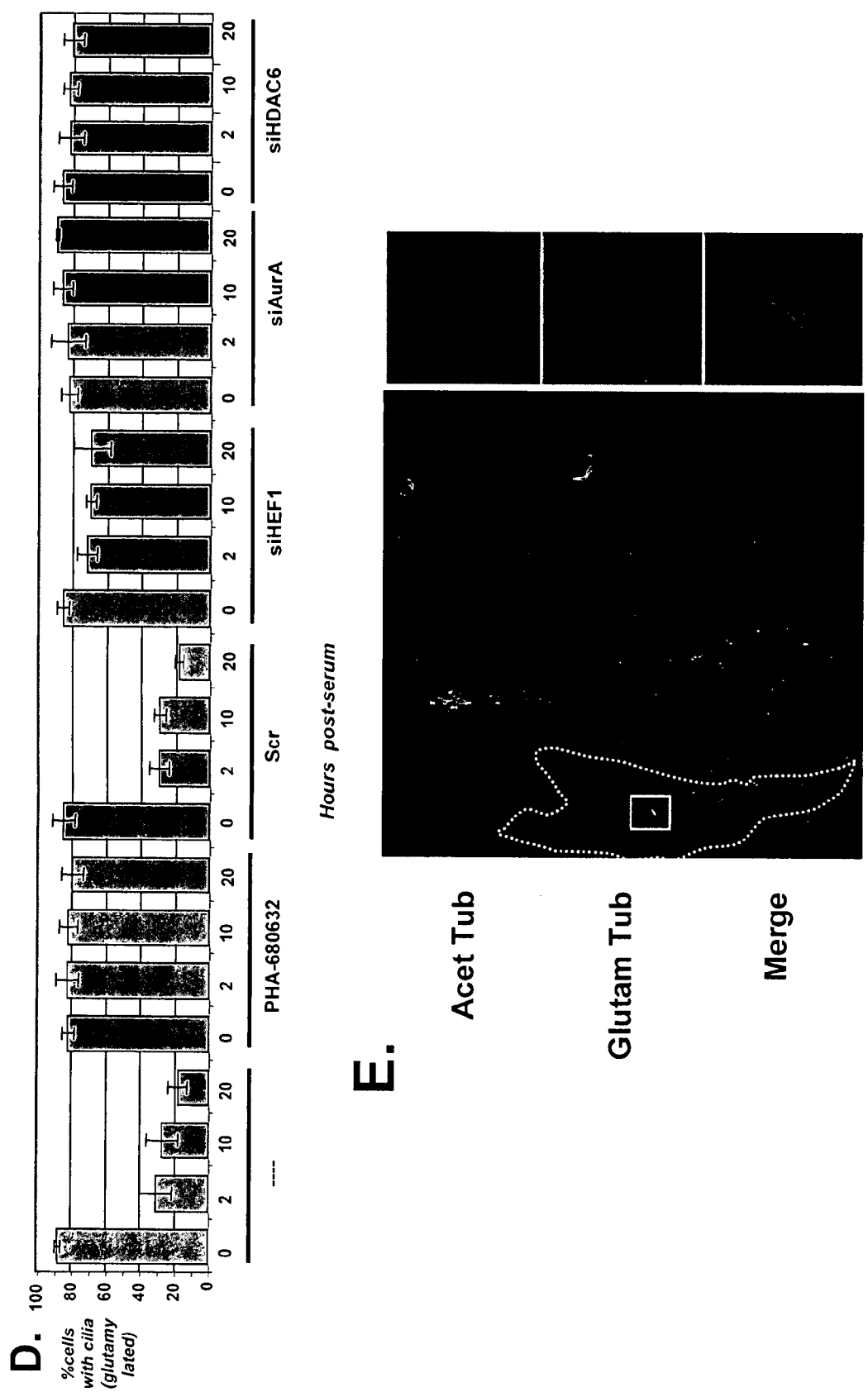
Figure 8:
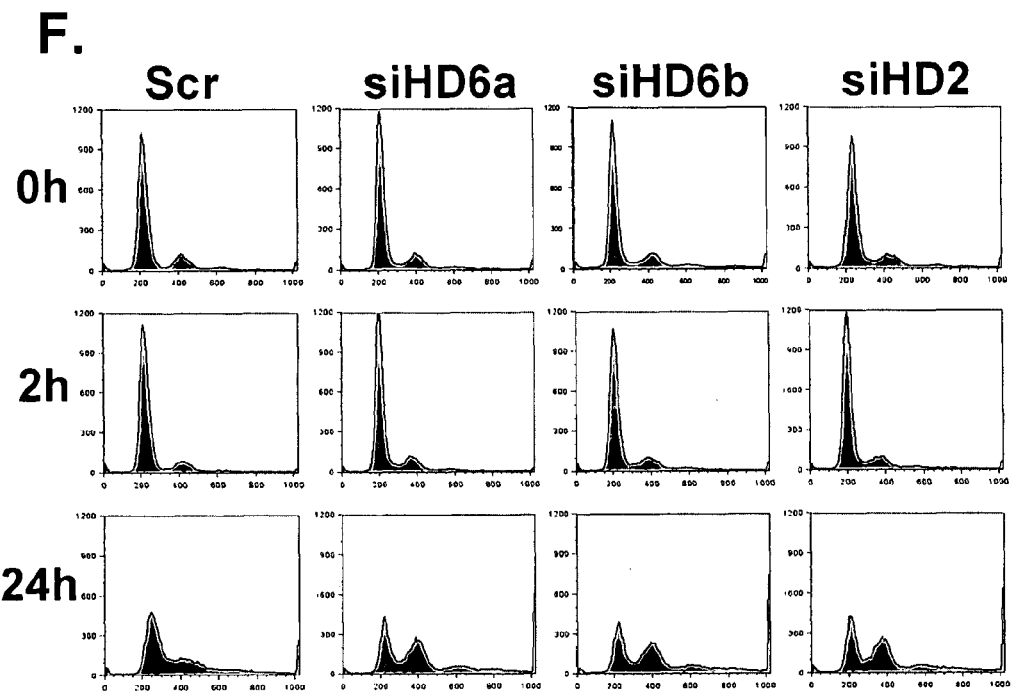
Figure 8:
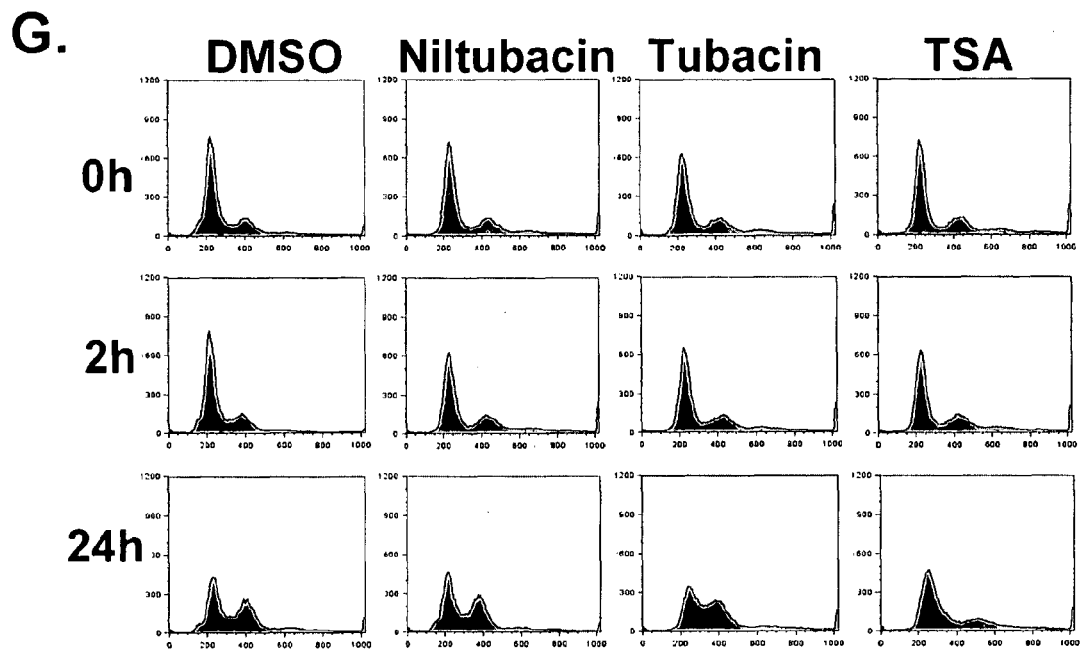

FIG. 8. Depletion and FACS Profiles of hTERT-RPE1 Cells Treated with siRNAs or Small Molecules.

A. hTERT-RPE1 cells were treated with siRNA to AurA or HEF1, and protein depletion visualized by Western analysis. SiRNAs used were Ambion Cat. #44607 and 44668 for HEF1, and Dharmacon Cat. #D-003545-02 for AurA. B. Immunoprecipitates from experiments described in FIG. 3B were probed with antibody to AurA, C. FACS analysis of cells pre-depleted with siRNA to HEF1 or to AurA, or scrambled control (Scr) siRNA, at the times indicated after serum stimulation. D. Time course and degree of ciliary resorption assessed by scoring cells treated with siRNAs and inhibitors as indicated, based on visualization after staining with antibody to glutamylated tubulin. E. Cilia visualized with antibody to both acetylated a-tubulin (red) and glutamylated a-tubulin (blue), indicating equivalent staining. F. FACS analysis of cells pre-depleted with two siRNAs for HDAC6 (siHD6a, b), siRNA to HDAC2 (siHD2), or control scrambled (Scr) siRNA at the times indicated after serum stimulation. G. FACS analysis of cells pre-treated with DMSO vehicle, niltubacin, tubacin, or TSA, at the times indicated after serum stimulation.

Figure 9:
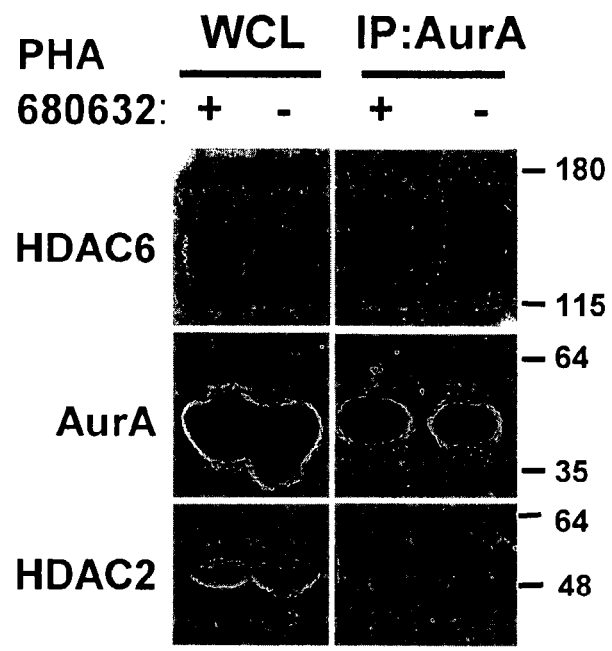
Figure 9:
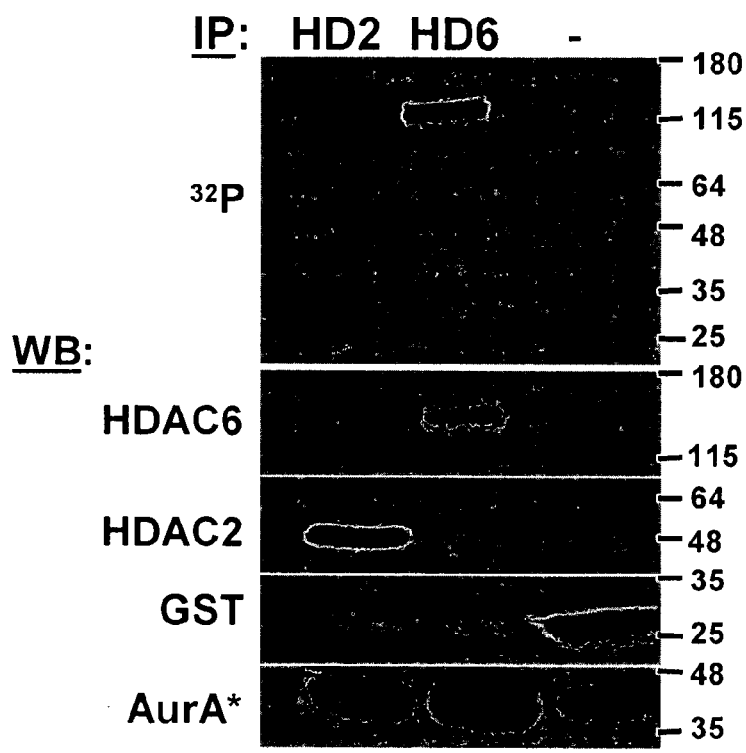
Figure 9:
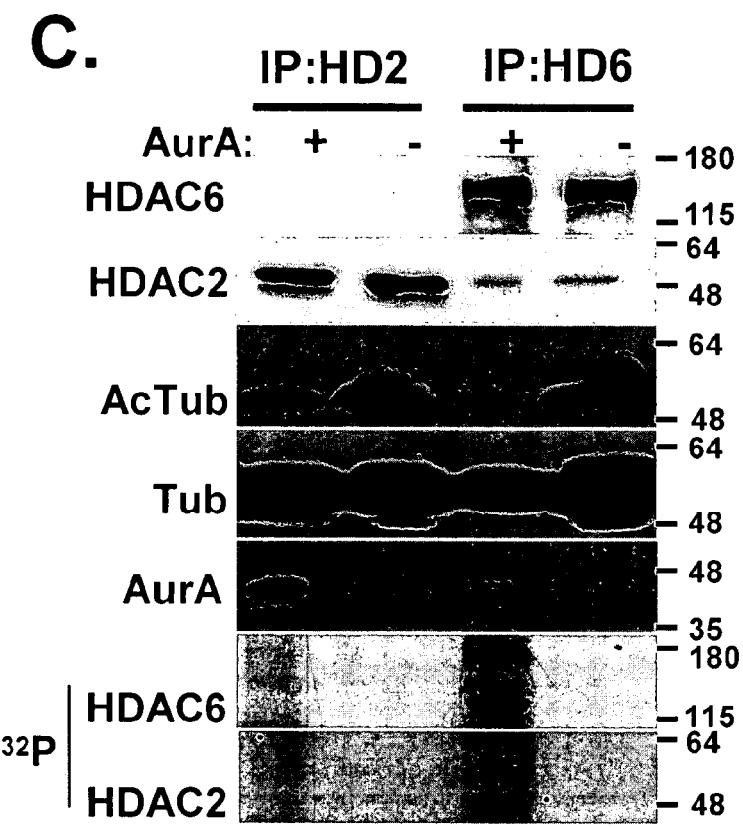
Figure 9:
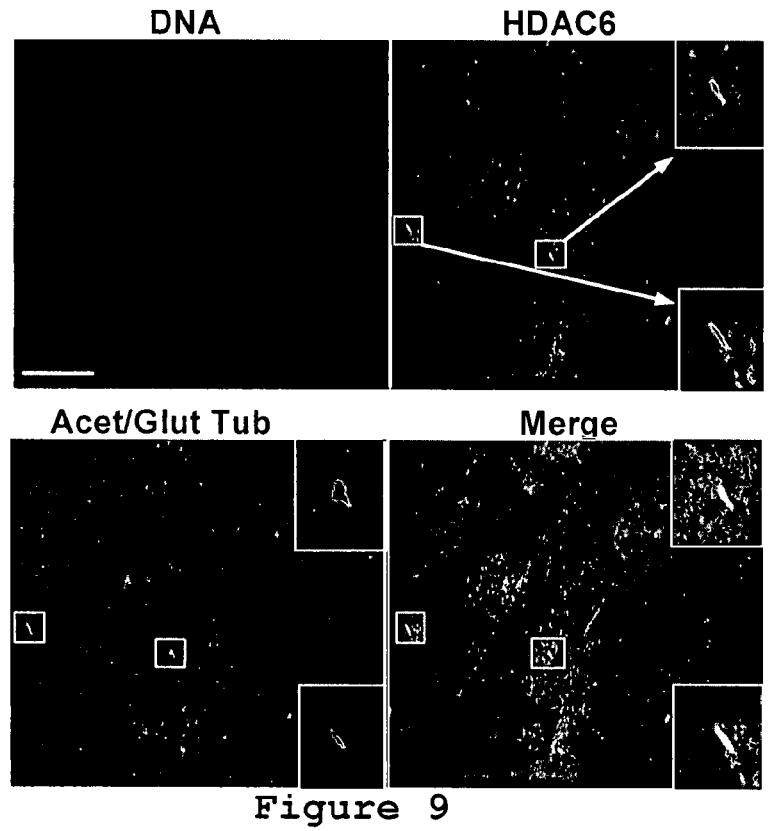

FIG. 9, Direct Phosphorylation by AurA Activates HDAC6 Tubulin Deacetylase Activity.

A. hTERT-RPE1 whole cell lysate (WCL) of cells treated with AurA inhibitor PHA 680632 (+) or with vehicle (−) was analyzed by Western blot directly, or following immunoprecipitation (IP) with antibody to AurA, using antibodies as indicated. The immunoprecipitation of the slow-migrating form of HDAC6 is not impacted by treatment of cells with PHA-680632, indicating that it most likely represents HDAC6 modified by an additional (unknown) cellular kinase/s. B. AurA phosphorylates HDAC6. In vitro translated and immunoprecipitated HDAC2 or HDAC6 (HD2, HD6), or recombinant GST (−), were mixed with recombinant AurA and used in an in vitro kinase assay. Reaction was split and used for autoradiography ($^{32}$P) or Western Blot (WB) C. In vitro translated HDAC2 or HDAC6 (HD2, HD6) were immunoprecipitated (IPed). IPs were mixed with AurA (+) or buffer (−), then used for either an in vitro tubulin deacetylation assay, or in an in vitro kinase assay using γ-$^{32}$P-ATP. Reaction mix was visualized by Western blot and by autoradiography, as indicated. D. HDAC6 localizes to disassembling cilia 2 hours after serum treatment. Scale bar, 15 μM.

Figure 10:
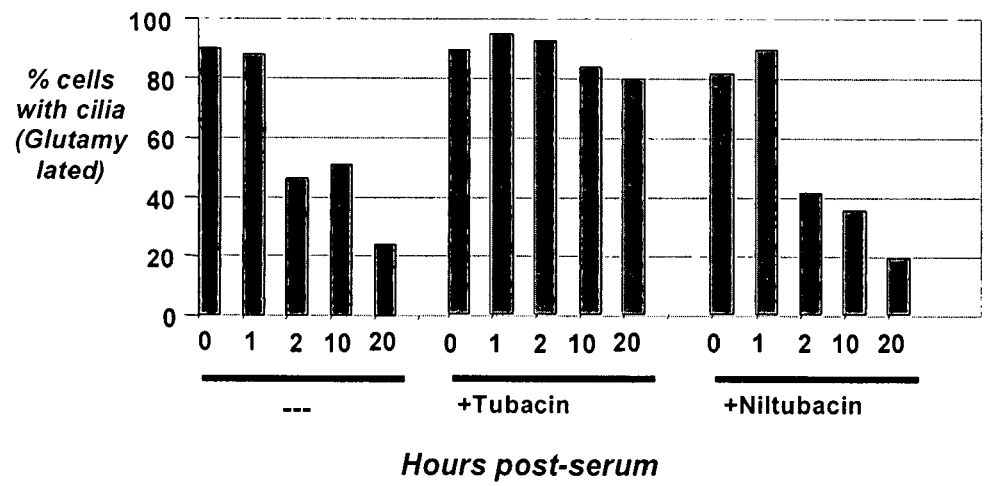
Figure 10:
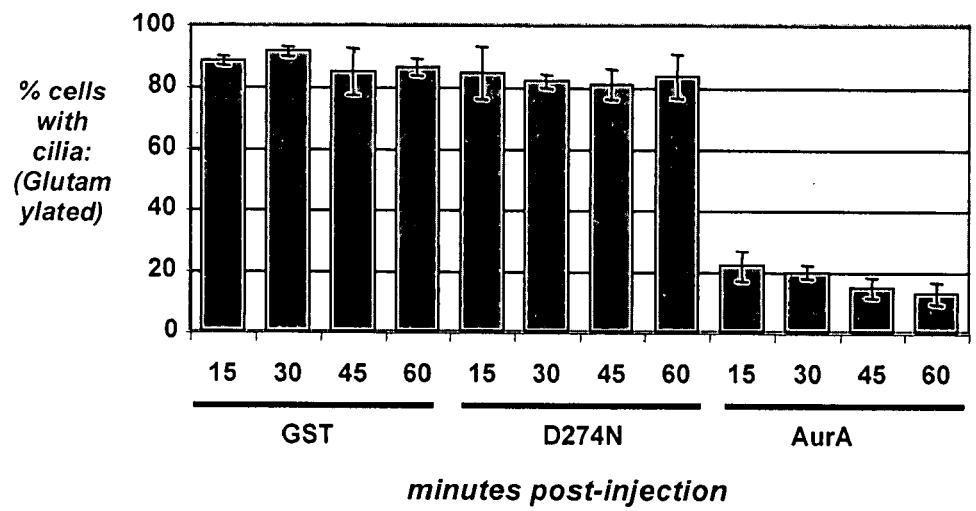
Figure 10:
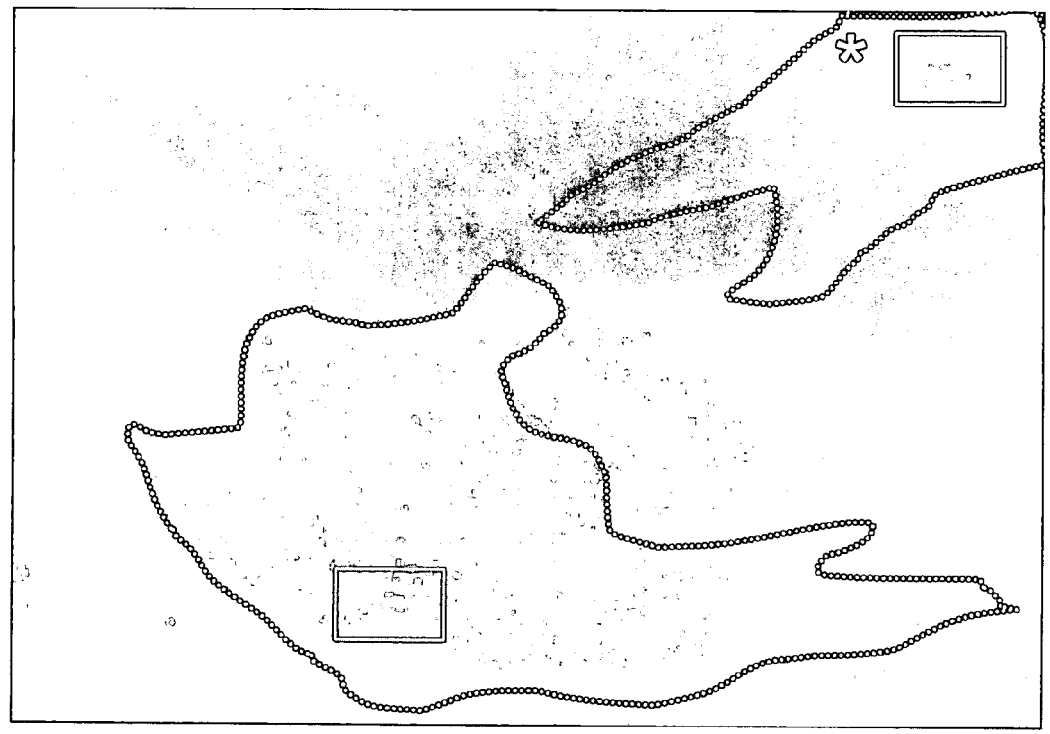
Figure 10:
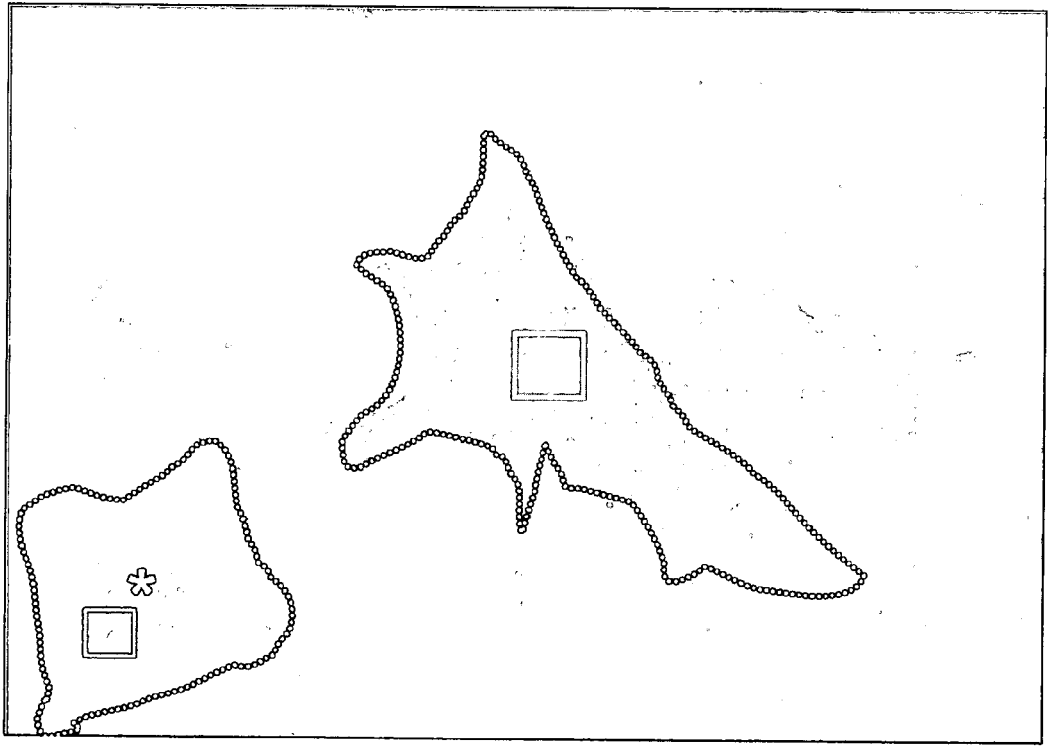

FIG. 10. Disassembly of Cilia Visualised with Antibody to the Ciliary Marker Glutamylated Tubulin (1:250, Sigma).

A. Time course and degree of ciliary resorption assessed by scoring cells treated with tubacin and niltubacin as indicated, based on visualization after staining with antibody to glutamylated tubulin. B. Experiment as in A., with cells microinjected with AurA, D274D, and GST. C. Staining with α-acetylated α-tubulin (red) and glutamylated tubulin (blue) indicates microinjection of AurA (marked by Dextran488, green) induces loss of signal at cilia during ciliary disassembly (boxes shown at high magnification to right; compare with uninjected cells, *). In contrast, AurA injection does not influence α-acetylation of cytoplasmic microtubule networks.

Figure 11:
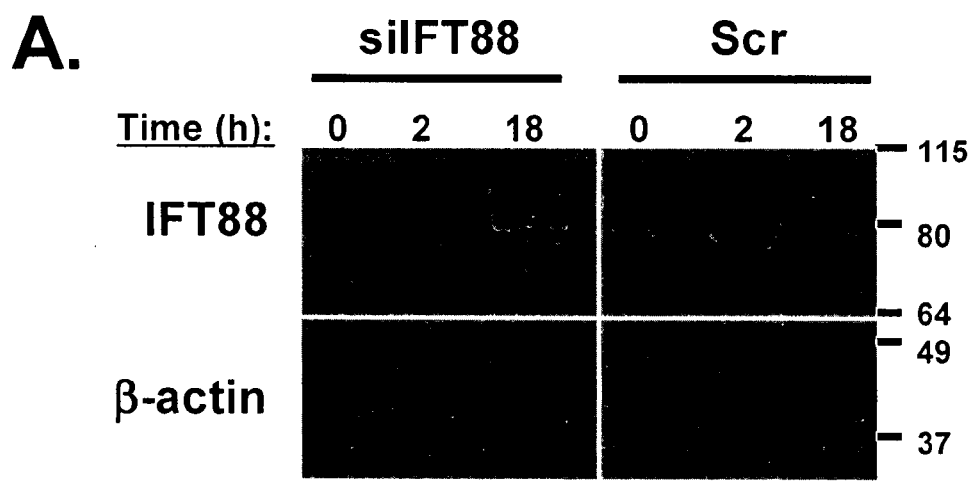
Figure 11:
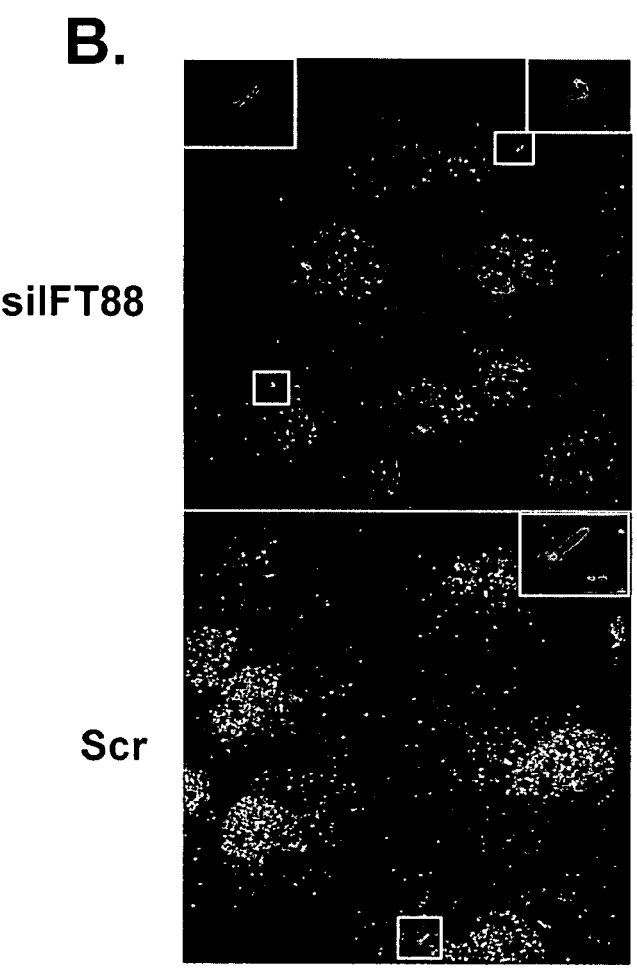
Figure 11:
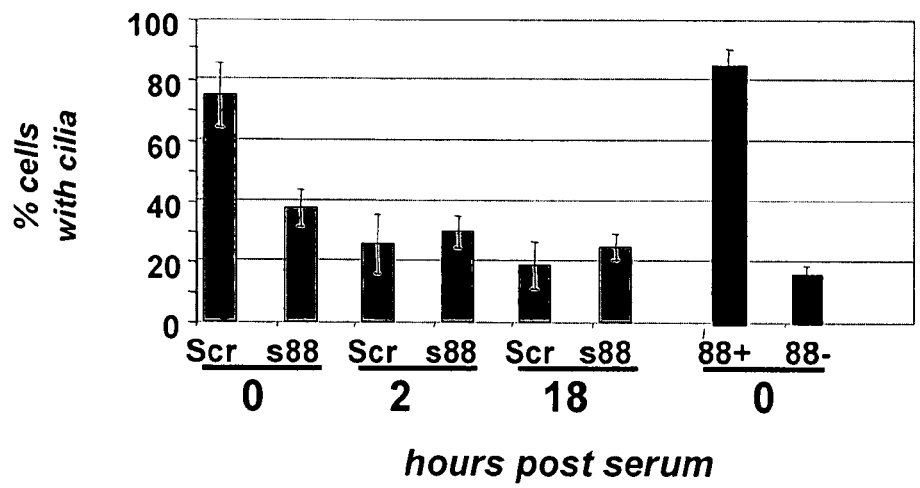
Figure 11:
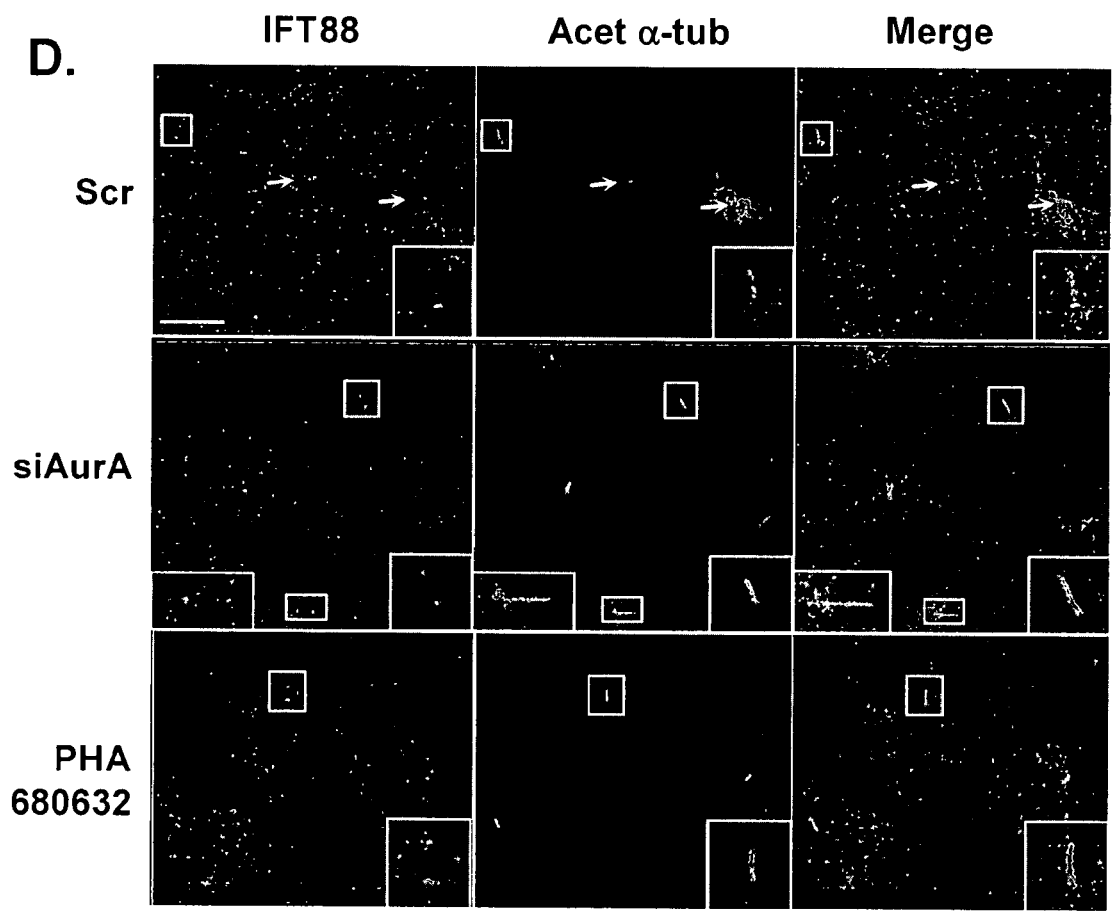

FIG. 11. A Role for IFT Proteins in AurA-Induced Ciliary Resorption.

A. Western blot demonstrating siRNA depletion of IFT88 (siIFT88) in ciliated hTERT-RPE1 cells at times following serum treatment, relative to scramble-depleted control, B. Immunofluorescence matching FIG. 11A at time 0, indicating relative degree of depletion of IFT88 at the basal body. C. Ciliary disassembly in IFT88-depleted (s88) versus Scr-depleted cells, at 0, 12, or 18 hours after serum treatment, based on the total cell population (gray bars). Black bars (right) indicate % ciliated cells at time 0 calculated specifically from cells confirmed by immunofluorescence to have significant IFT88 staining (88+), or to be well-depleted for IFT88 (88−). D. Cells treated with scrambled (Scr) or AurA-targeting (siAurA) siRNAs, or with PHA-680632 were fixed 2 hours after serum-initiated disassembly. Shown, immunofluorescence indicating cilia (anti-acetylated α-tubulin, red) and IFT88 (green). Insets are enlargements of boxed ciliary structures; arrows indicate direction of ciliary projection relative to basal body. Scale bars, 10 μm.

Figure 12:
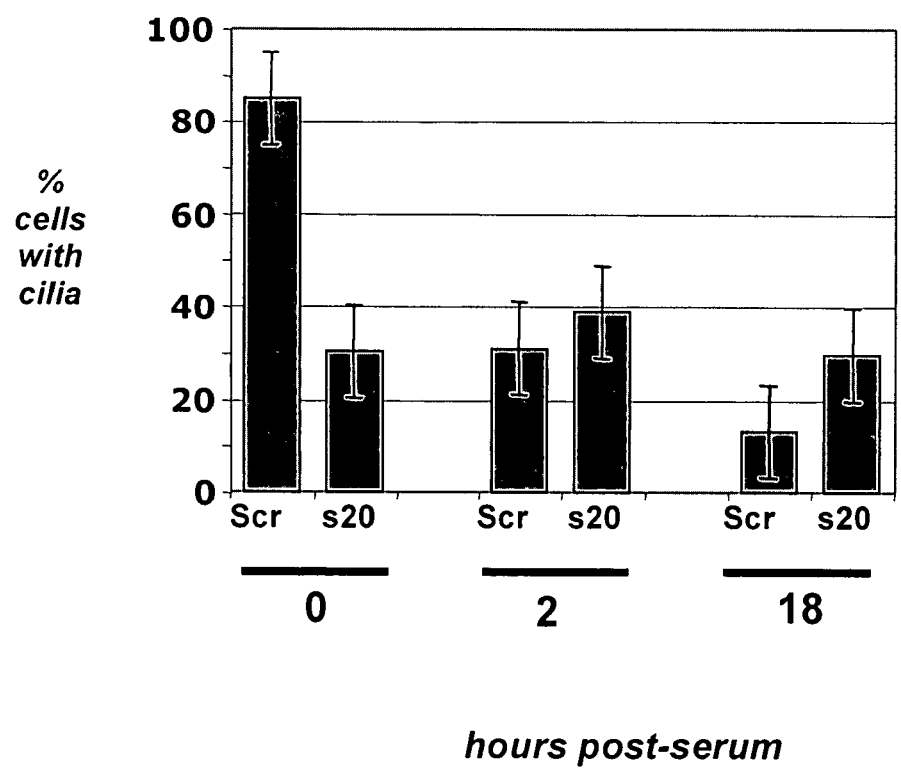

FIG. 12. Ciliary Disassembly in IFT20-(s20) Verses Scr-Depleted Cells.

Figure 13:
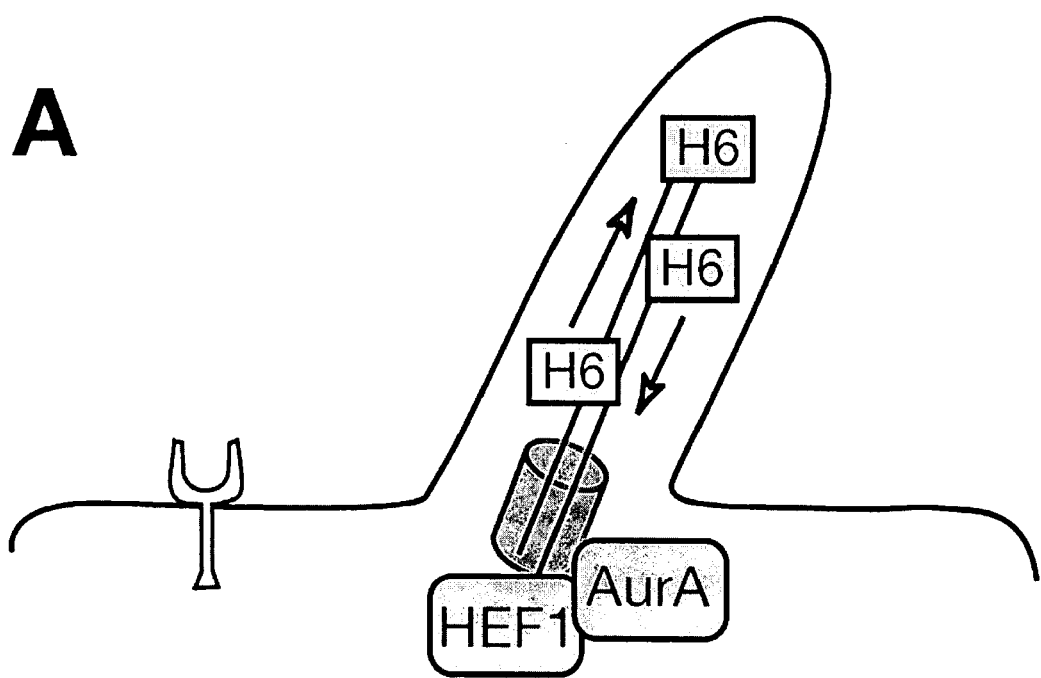
Figure 13:
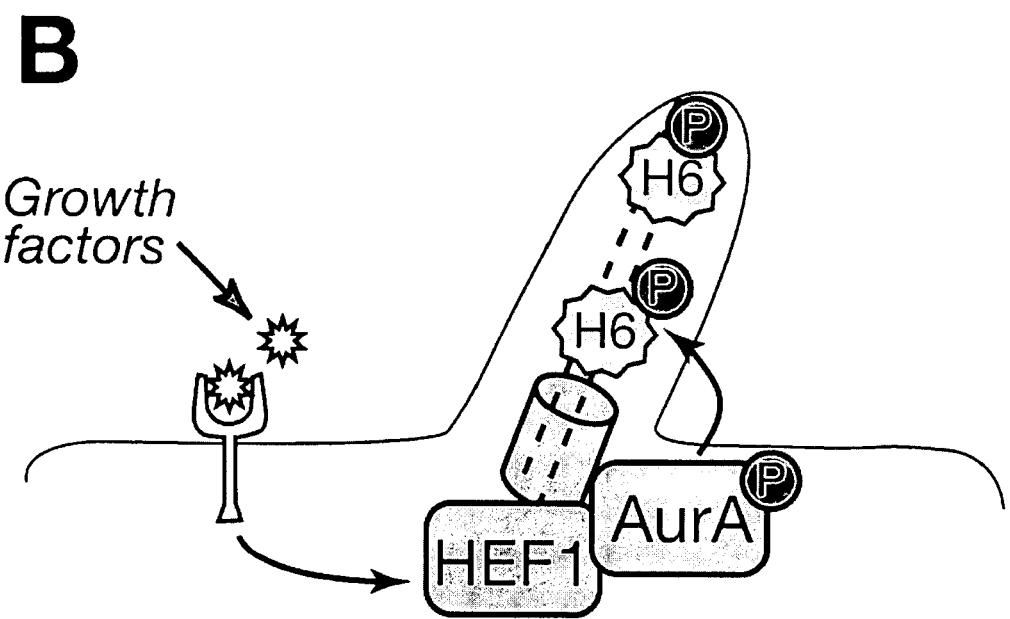

FIG. 13. Working Model.

A. Aurora A (AurA) and HEF1 are localized to the basal body of quiescent, ciliated cells. B. Our data are consistent with a model in which growth factors induce HEF1 expression, promoting HEF1-dependent activation of Aurora A. This results in phosphorylation of ciliary HDAC6 (H6) by Aurora A, thereby inducing ciliary resorption.

Figure 14:
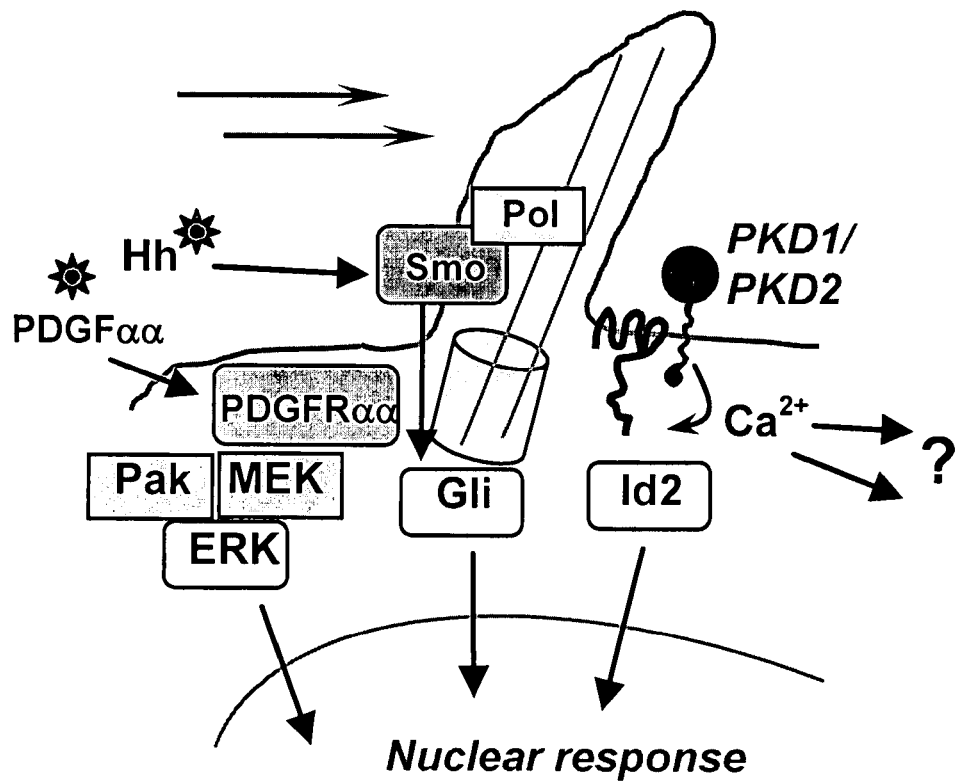

FIG. 14. Flow Induced Mechanosensation and Diffusible Factors Promote Signaling at Cilia.

Stimulation of poly-cystins 1 and 2 induces $Ca^{2+}$ influx, activating Id2 and other effectors. Hedgehog (Hh) activation of its effector Gli requires Polaris (Pol) to anchor the Smoothened (Smo) receptor at the cilium. Similarly, PDGFαα interacts with its receptor at cilia to activate MEK and ERK, with contributions from Pak.

Figure 15:
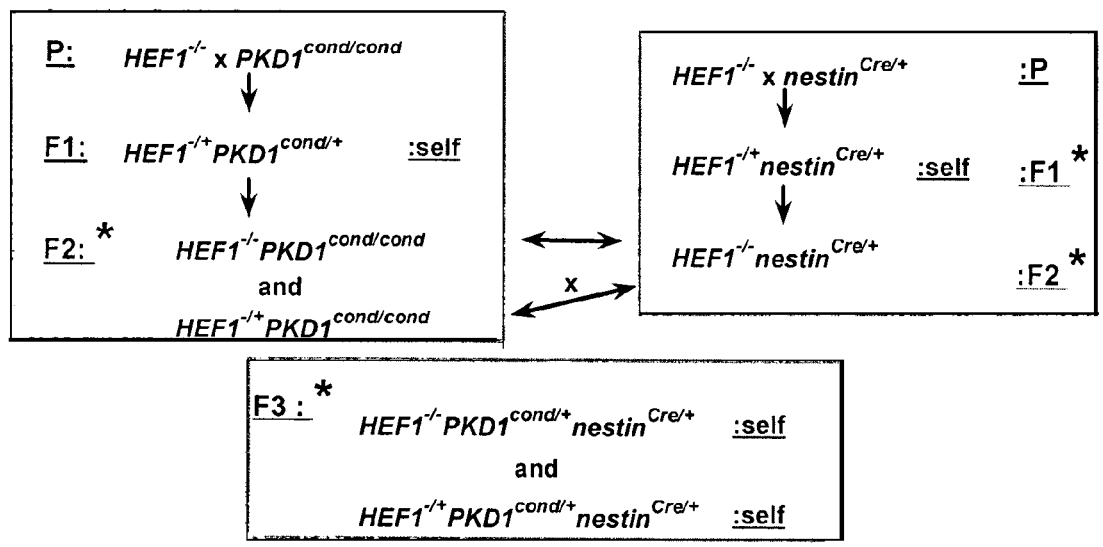

FIG. 15. Outline of Crosses to Generate Mice for Exploring Efficacy of Agents for the Treatment of Disorders Related to Aberrant Cilia Assembly and Disassembly, Particularly PKD.

Progeny from F3 brother-sister matings will have the genotypes shown. *Only the genotypes of animals to be used in subsequent mating steps are shown.

DETAILED DESCRIPTION OF THE INVENTION

The mammalian cilium protrudes from the apical/lumenal surface of polarized cells, and acts as a sensor of environmental cues. Numerous developmental disorders and pathological conditions have been shown to arise from defects in cilia-associated signaling proteins. Despite mounting evidence that cilia are essential sites for coordination of cell signaling, little is known about the cellular mechanisms controlling their formation and disassembly. Here we show that defined interactions between the pro-metastatic scaffolding protein HEF1/Cas-L/NEDD9 and the oncogenic Aurora A (AurA) kinase at the basal body of cilia causes phosphorylation and activation of HDAC6, a tubulin deacetylase, promoting ciliary disassembly. We show that this pathway is both necessary and sufficient for ciliary resorption, and constitutes an unexpected non-mitotic activity of AurA in vertebrates. Moreover, we demonstrate that small molecule inhibitors of AurA and HDAC6 selectively stabilize cilia from regulated resorption cues, suggesting a novel mode of action for these clinical agents.

The following definitions are provided to facilitate an understanding of the present invention:

Disorders associated with aberrant cilia function and regulation include, without limitation, polycystic kidney disease (PKD), Bardet-Biedl Syndrome (BBS), renal cysts, infertility, respiratory disorders, situs inversus, and predisposition to obesity, diabetes, and hypertension.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like. The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

"Native" refers to a naturally occurring ("wild-type") nucleic acid sequence.

"Heterologous" sequence refers to a sequence which originates from a foreign source or species or, if from the same source, is modified from its original form.

A "coding sequence" or "coding region" refers to a nucleic acid molecule having sequence information necessary to produce a gene product, when the sequence is expressed.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The DNA used for altering a target gene may be obtained by a wide variety of techniques that include, but are not limited to, isolation from genomic sources, preparation of cDNAs from isolated mRNA templates, direct synthesis, or a combination thereof.

The examples set forth below are provided to exemplify certain embodiments of the invention. They are not intended to limit the invention in any way.

Example I

We demonstrate that an association between AurA and HEF1 at cilia in response to extracellular cues is required for ciliary disassembly. We also show that AurA activation is independently sufficient to induce rapid ciliary resorption, and that AurA acts in this process through phosphorylating HDAC6, thus stimulating HDAC6-dependent tubulin deacetylation (Hubbert et al., 2002) and destabilizing the ciliary axoneme. Importantly, our identification of a spatiotemporally restricted action of AurA at the ciliary basal body in cells emerging from G0 demonstrates an unexpected non-mitotic activity for AurA in vertebrate cells. We also determine that small molecule inhibitors of AurA and HDAC6 reduce regulated disassembly of cilia, which may have important implications for the action of these drugs in the clinic. Together, these data reveal important activities for HEF1, AurA, and HDAC6 in regulation of ciliary resorption, which should also inform the actions of these proteins in cell cycle and cancer (Hideshima et al., 2005; Kim et al., 2006; Marumoto et al., 2005; Pugacheva and Golemis, 2005).

The following materials and methods are provided to facilitate the practice of the present invention.

Cell Culture and siRNA.

hTERT-RPE1 cells were grown in DMEM with 10% fetal bovine serum (FBS). For analysis of ciliary disassembly, cells were plated at 30% confluence in plates containing glass cover slips, and starved for 48 hours (in Opti-MEM or regular DMEM, without added serum) to induce cilia formation, followed by treatments described hereinbelow. For siRNA treatment, cells were initially plated in DMEM/10% FBS in plates containing cover slips, and 12 hours later siRNA transfection was performed in Opti-MEM with Oligofectamine (Invitrogen) according to manufacturer recommendations, and fixed 48 hours after transfection, following treatments indicated in Results. The remaining cells on plate were lysed, then either directly analyzed by Western blot analysis, or used for immunoprecipitation (IP)-kinase reaction to measure AurA activity.

For RNA interference (RNAi)-induced depletion of HEF1 and AurA, 2 independent, synthetic duplex siRNAs were used for each gene: 1) Ambion, cat#16704, NEDD9, ID:17729, sense 5'GGUAUAUCAGGUGCCACCAtt3' (SEQ ID NO: 1); 2) Dharmacon, custom, sense: 5' AAGGGGUAUAUGC-CAUUCCGCdTdT 3'$^{57}$ (SEQ ID NO: 2). Non-specific control siRNAs including scrambled (Dharmacon, cat#D-001206-13-05) and GFP-directed sequences (Dharmacon, cat#D-001300-01-20) were used for reference.

Drug Inhibition Experiments.

The Aurora kinase inhibitor PHA-680632, GSK3□-inhibitor 1 (Calbiochem), FTI-277 (Calbiochem), Tubacin, Niltubacin or DMSO vehicle were added to hTERT-RPE1 cells 2 hours prior to the initiation of ciliary disassembly. After initial titration experiments to establish effective range, PHA-680632 was used at 0.5 µM, Tubacin and Niltubacin at 2 µM, GSK3µ-inhibitor 1 at 2 µM, FTI-277 at 50 nM concentration for the experiments described.

Protein Expression, Western Blotting, and Immunoprecipitation.

For microinjection, recombinant glutathione-S-transferase (GST), GST fused AurA mutants T288A and D274N) produced from BL21 (DE3) bacteria were purified using the MicroSpin GST Purification Module (Amersham Biotech.). Purified recombinant AurA was purchased from Upstate; this AurA was pre-activated based on incubation with ATP. Mutationally inactive AurA (T288A,) was also made using a baculoviral expression system (Invitrogen), and was purified by Ni-Sepharose 6FF (Amersham). To prepare lysates for Western blotting and IP, mammalian cells were disrupted by M-PER lysis buffer (Pierce) supplemented with EDTA-free protease inhibitor cocktail (Roche). Lysates used for IP were incubated overnight with antibody at 4° C., subsequently incubated for 2 hours with protein A/G-sepharose (Pierce), washed, and resolved by SDS-PAGE. Western blotting was performed using standard procedures and proteins visualized using the West-Pico system (Pierce). Antibodies used included mouse monoclonal antibody (mAb) anti-HEF1 2G9 (Pugacheva and Golemis, 2005), anti-α-tubulin mAb (Sigma), anti-AurA (BD Bioscience) for Western blotting, anti-AurA rabbit polyclonal (Cell Signaling) for IP, anti-Phospho-AurA/T288 (BioLegend), anti-Phospho-AurA/T288 (Cell Signaling), anti-HDAC6 rabbit polyclonal (Upstate; 1:5000), anti-HDAC2 rabbit polyclonal (Invitrogen) and mAb anti-β-actin (AC15, Sigma), anti-IFT88 and anti-IFT20. Secondary horseradish peroxidase (HRP)-conjugated antibodies were from Amersham Biotech.

Immunofluorescence.

Cells were fixed with 4% paraformaldehyde (10 min) then methanol (5 min), permeabilized with 1% Triton-X100 in PBS, blocked in 1×PBS, 3% BSA, and incubated with antibodies using standard protocols. Primary antibodies included rabbit polyclonal anti-Aurora A and anti-phospho-AuroraA/T288, (Cell Signaling), mouse mAb anti-HEF1 (14A11), polyclonal anti-γ-tubulin (Sigma), anti-α-tubulin mAb (Sigma), anti-acetylated α-tubulin mAb (clone 6-11B-1, Sigma, and clone K(Ac)40 Biomol), anti-IFT88 and anti-IFT20 (gifts of G. Pazour), mouse anti-glutamylated tubulin (Sigma), and anti-HDAC6 (Upstate). Secondary antibodies labeled with Alexa-488, Alexa-568, and Alexa-633, and TOTO-3 dye to stain DNA, were from Molecular Probes/Invitrogen. DNA was co-stained in some experiments by propidium iodine (Sigma) or Draq5 (Alexis), Confocal microscopy was performed using a Radiance 2000 laser scanning confocal microscope ((Carl Zeiss, Thornwood, N.Y.) coupled to a Nikon Eclipse E800 upright microscope (Nikon). Statistical analysis of data by one-way ANOVA was performed using GraphPad Instat 3.0 (San Diego, Calif.).

Microinjection.

Microinjections were performed on a Nikon TE300 Microscope (Nikon, Melville, N.Y.) that was equipped with an Eppendorf Transjector 5246 semi-automatic microinjector and micromanipulator (Eppendorf, Westbury, N.Y.). Cells were plated on gridded coverslips (Belco) and starved for 48 hours before cytoplasmic microinjection of 0.05 µM pre-activated AurA (Upstate), inactive AurA (T288A) and (D274N), GST protein, or buffer. Proteins were pre-filtered through a 0.2-µm Milliopore membrane and mixed with Dextran Green488 (Molecular Probes) to mark injected cells. Injected cells were incubated at 37° C. before fixation. Typically, 150 cells were microinjected in each of 3 experiments.

Kinase and Tubulin Deacetylation Assays.

In vitro kinase assays were performed using recombinant active AurA (Upstate), mutationally inactive AurA purified from baculovirus and BL21 (DE3) bacteria, or endogenous AurA immunoprecipitated from mammalian cells. A standard kinase reaction with γ-$^{32}$P(ATP) and histone H3 and MBP (Upstate) substrates was done as in (Pugacheva and Golemis, 2005). For deacetylase assays, HDAC6 and HDAC2 were in vitro translated using a TnT-Coupled Reticulocyte Lysate System (Promega), immunoprecipitated, and incubated with/without active AurA (Upstate) in the presence of (25 µg) stabilized microtubules prepared from purified bovine brain tubulin (Cytoskeleton) to measure deacetylase activity (as in (Hubbert et al., 2002)) and with γ-$^{32}$P-ATP (Perkin-Elmer) in AurA reaction buffer. 1/10 volume of samples were reserved for Western blotting.

Results

A System for Regulated Ciliary Assembly and Disassembly

Figure 1:
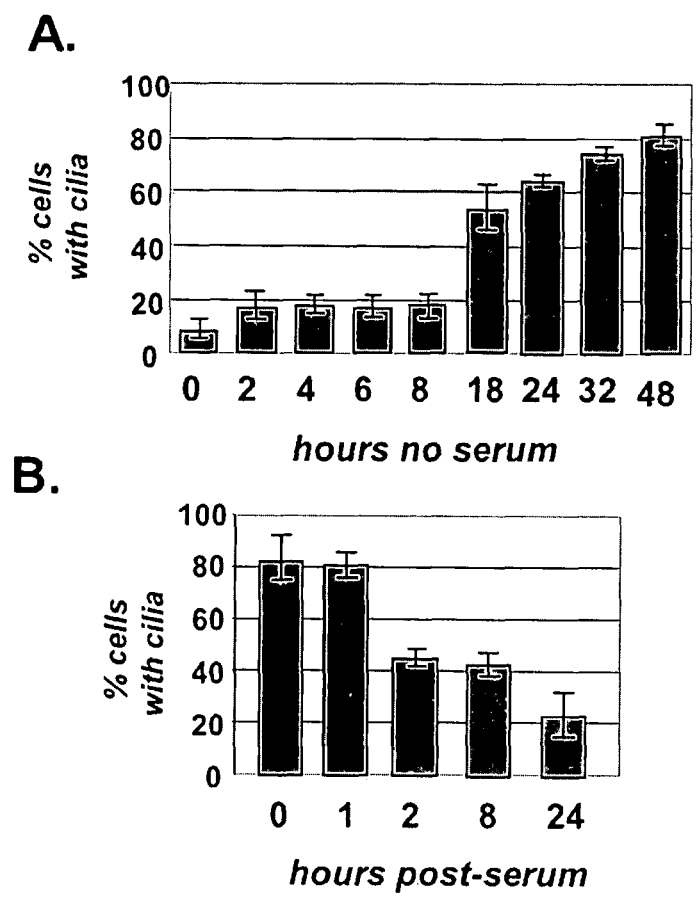
FIG. 1. Activation of AurA at the Basal Body Occurs During Ciliary Disassembly.
Figure 1:
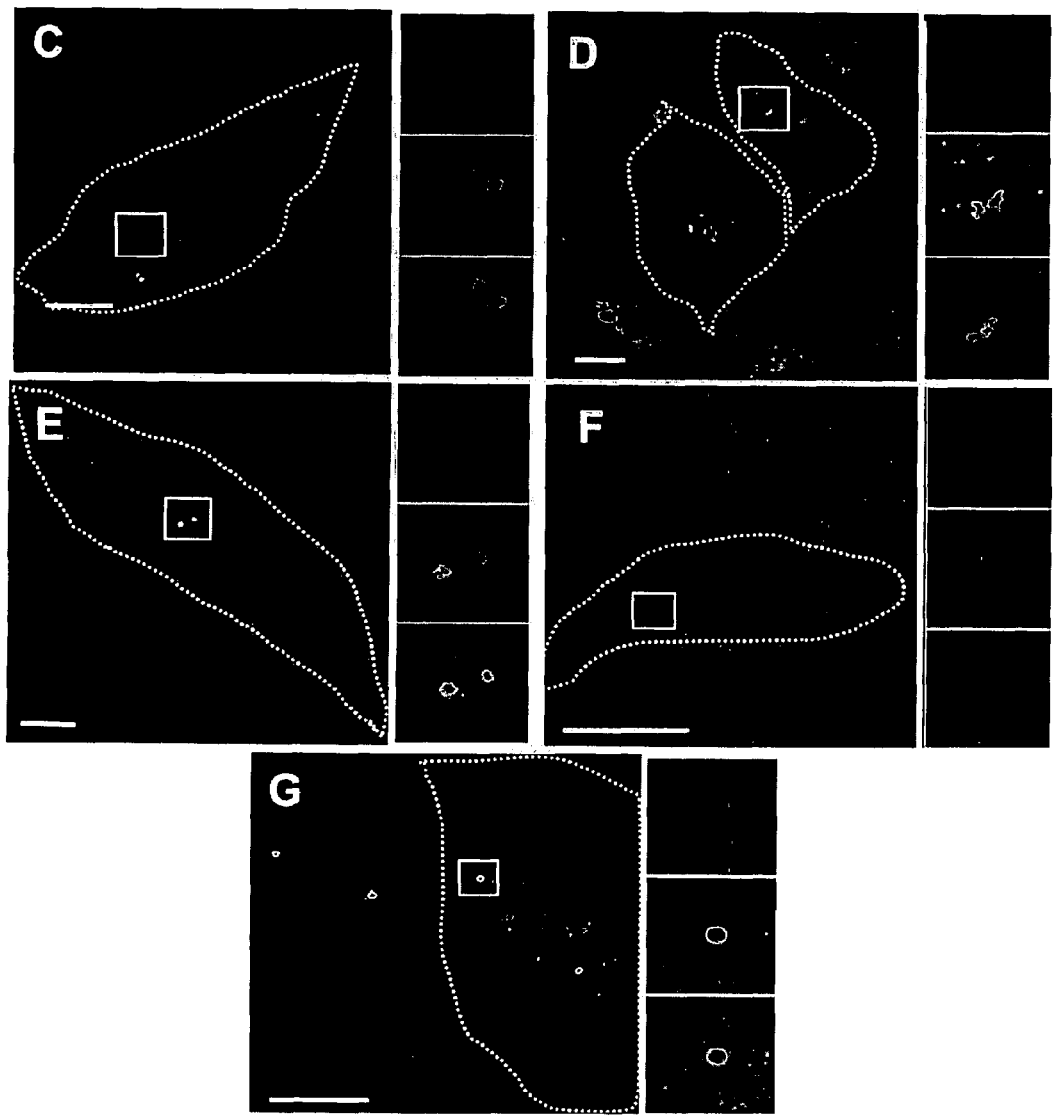
Figure 1:
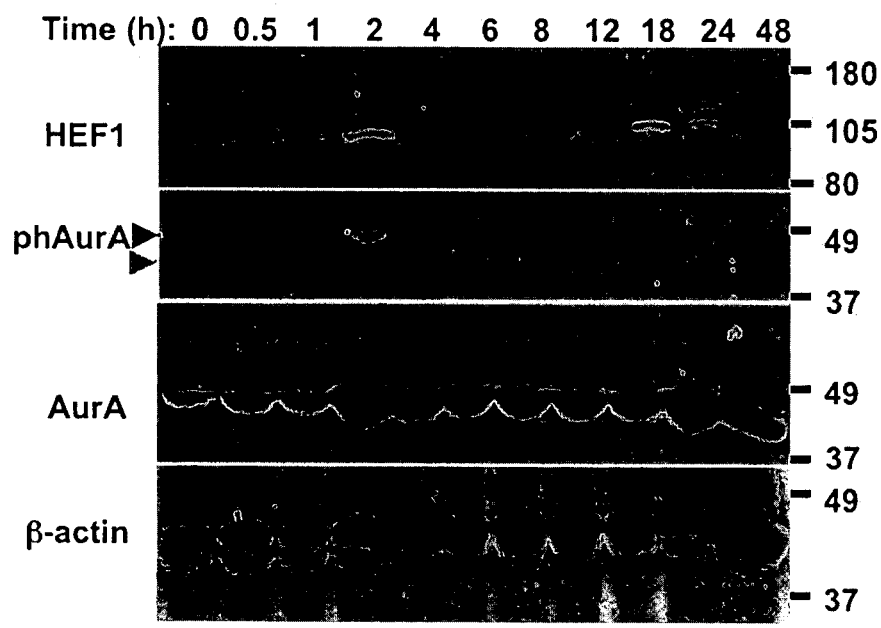
Figure 1:
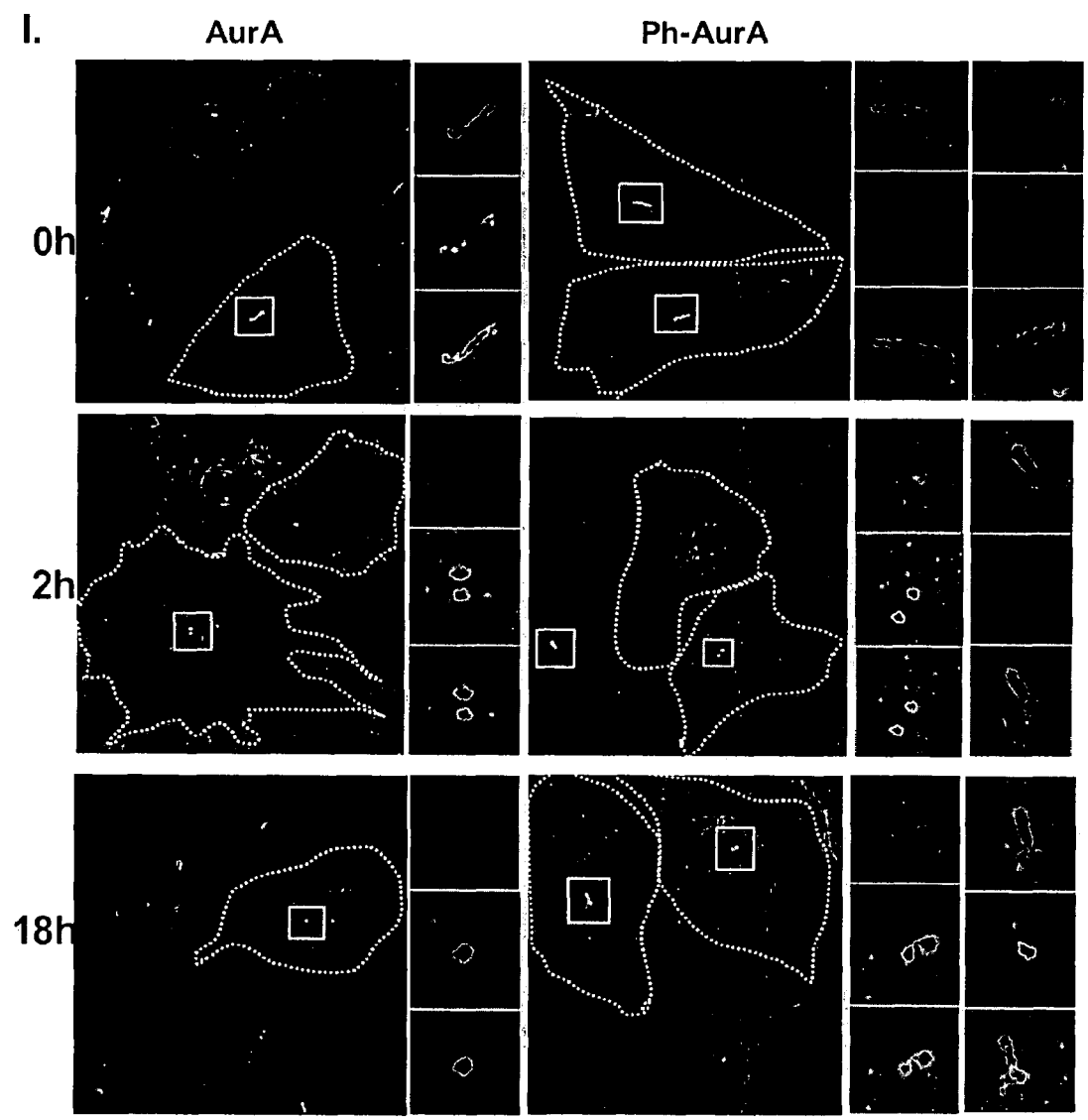

We established a system to study ciliary dynamics in the hTERT-RPE1 cell line. 48 hours after plating cells at 50-70% confluence in Opti-MEM medium without serum, >80% of hTERT-RPE1 cells had clearly visible cilia (FIG. 1A). Cilia were typically of 3-4 µm length, with an acetylated α-tubulin-marked axoneme adjacent to two γ-tubulin-positive structures reflecting the basal body and the second cellular centriole. See FIG. 2A. Treatment of these ciliated cells with medium containing 10% fetal bovine serum (FBS) caused ciliary disassembly over the following 24 hours (FIG. 1B). This disassembly occurred in two waves, with the first occurring 1-2 hours after serum stimulation, and the second after 18-24 hours. FACS analysis, BrDU staining, and observation of condensed DNA and mitotic figures indicated that cells remained predominantly in G1 phase at 2 hours post-serum addition, while during the 18-24 hour disassembly wave, most cells were entering mitosis (FIGS. 2B, 2C). This disassembly behavior was not unique to hTERT-RPE1 cells, as we observed a comparable biphasic resorption profile in the IMCD-3 murine and Caki-1 human renal cell lines (FIGS. 2D, 2E). To begin to assess serum components that might regulate ciliary disassembly, we have assessed PDGF, TGF-β, and EGF (FIG. 4). Of these, only PDGF elicited a partial response. Full disassembly likely requires the combined input of several distinct serum components.

Dynamic Regulation of HEF1 and AurA at the Basal Body During Ciliary Disassembly.

AurA (FIG. 1C) and HEF1 (FIGS. 1D,E) localized to the basal body and the second centriole in quiescent, ciliated hTERT-RPE1 cells. In contrast, activated ($T^{288}$-phosphorylated) AurA was not detected at basal bodies of cilia in quiescent cells (FIGS. 1F, 1I (0 h)) under fixation conditions at which it was clearly evident in mitotic cells (FIG. 1G).

If AurA were functionally important for ciliary disassembly, we would expect changes in the activity of AurA 1-2 hours after serum treatment, potentially accompanied by changes in the AurA activator HEF1, Indeed, HEF1 expression increased at 1-2 hours after serum stimulation, dropped, and peaked again at ~18-24 hours after serum stimulation (FIG. 1H). HEF1 initially appeared as a faster migrating 105 kD species, with a slower migrating 115 kD species appearing later. This 115 kD species represents S/T-phosphorylated HEF1, is most, abundant during the G2/M compartment in actively cycling cells, and is associated with AurA activation (Law et al., 1998; Pugacheva and Golemis, 2005). Total AurA levels sometimes increased slightly at 2 hours post-serum stimulation, but were largely unaffected (FIG. 1H). In contrast, peaks of phospho-$T^{288}$-AurA appeared precisely at each of the two waves of ciliary disassembly (FIGS. 1H, I). Strikingly, phospho-$T^{288}$-AurA was almost never detected at a basal body near a well-formed cilium. Although phospho-$T^{288}$-AurA invariably co-localized with both γ-tubulin-marked basal bodies/centrioles and with total AurA, in 85-90% of cells with phospho-$T^{288}$-AurA, centrioles had no accompanying cilium. In 10-15% of cells with phospho-$T^{288}$-AurA, centrioles with adjacent acetylated α-tubulin-marked cilia were observed, but these cilia were significantly shortened (~1-2 versus 3.5 μm) (FIG. 1I). Similar profiles of HEF1 and AurA expression and activation were observed in serum-treated IMCD3 and Caki-1 cells, and PDGF-treated hTERT-RPE1 cells (FIGS. 3B, 3C, 3F, 3G). The simplest interpretation of these results is that activation of AurA at the basal body immediately precedes the rapid disassembly of cilia.

HEF1-Dependent Activation of AurA Induces Ciliary Disassembly.

We used two complementary approaches to establish that AurA activation is necessary and sufficient for induction of ciliary disassembly, and that HEF1 is likely to contribute to this process. First, exponentially growing hTERT-RPE1 cells were treated with siRNA targeting AurA or HEF1, or with control siRNA, plated for 2 days in OptiMEM to allow cilia formation, then treated with serum to induce ciliary disassembly. Immunoblotting confirmed siRNA treatment efficiently depleted AurA and HEF1 (FIG. 8A). AurA depletion blocked and HEF1 depletion greatly limited serum-induced disassembly (FIG. 3A). AurA activation was substantially reduced in cells treated with siRNA to HEF1 (FIG. 3B); this correlated with reduced levels of AurA in HEF1-depleted cells (FIG. 8B), implying HEF1 contributes to AurA stabilization as well as activation. Particularly at the second wave of ciliary disassembly, the residual cilia in HEF1-depleted cells were significantly longer than those in control cells (FIG. 3C), implying that HEF1 modulates the disassembly process. Importantly, cells treated with siRNA to AurA or HEF1, or with control siRNA, were all ~80% ciliated before addition of serum, leading us to conclude that the predominant role for HEF1 and AurA is at the time of disassembly, i.e., these proteins are not required to form cilia.

Second, we used the small molecule AurA kinase inhibitor PHA-680632 (Nerviano Medical Sciences (Soncini et al., 2006)) to inactivate AurA kinase (FIGS. 3D,E). Disassembly of cilia was strongly reduced in cells pre-treated for 3 hours with 500 nM PHA-680632 (FIG. 3D). Although some ciliary disassembly was observed at 1 and 2 hours after serum stimulation, the percentage was lower than in DMSO-treated cells, and disassembly was not maintained, with cilia consistently re-established at the 8- and 12-hour time points. The second wave of ciliary disassembly, at the time of mitosis, was completely eliminated in PHA-680632-treated cells (FIG. 3D). In cells with inhibited AurA, hyper-phosphorylated HEF1 did not accumulate significantly at either wave of ciliary disassembly, indicating AurA dependence of this phosphorylation (FIG. 3E). Western blot (FIGS. 3E, 3F (right panels)), in vitro kinase assays (FIG. 3F, left panels) and immunofluorescence (FIG. 3G) confirmed the effectiveness of the compound in blocking AurA activation.

Together, these data imply that activation of AurA by HEF1 contributes to resorption of cilia at 2 and 18 hours following serum stimulation (FIG. 3A-E) and that active AurA is necessary to stably complete the disassembly process, but that HEF1 may not be the sole factor driving AurA activation and ciliary resorption (FIG. 3A). Further, FACS analysis of cells with siRNA-depleted HEF1 or AurA (FIG. 8C), or drug-inhibited AurA (FIG. 3H) AurA indicated that the blocked resorption of cilia at the 2 h time point does not reflect an indirect consequence of altered cell cycle compartmentalization due to AurA inhibition. Cells indeed show predictable siRNA- and drug-induced accumulation in G2 at 18-24 h after serum stimulation, which may account for the reduced resorption at these time points. However all cells at 2 h post-serum treatment have similar cell cycle profiles, remaining predominantly in G0/G1. Hence, the role of HEF1 and AurA at this early non-mitotic time point represents an unexpected direct action of these proteins.

AurA Activation is Sufficient to Induce Rapid Disassembly of Cilia.

Next, as a direct approach to establish sufficiency of active AurA to induce disassembly, we microinjected pre-activated wild type AurA (aAurA), T288A AurA (a hypomorphic mutant, (Satinover et al., 2004)), D274N AurA (an inactive mutant), GST, or buffer alone, together with fluorescent marker dye, into hTERT-RPE1 cells with pre-formed. cilia. Microinjection of aAurA rapidly induced the disappearance of cilia from cells maintained in low serum medium: Essentially as soon as cells could be fixed after microinjection, more than 80% of injected cells lacked cilia (FIGS. 5A, 5B). In contrast, injection of GST or buffer did not Induce loss of cilia. Of the two mutants, D274N did not induce loss of cilia, while T288A caused eventual partial loss of cilia (FIG. 5A) and ciliary shortening (results not shown). The ability of aAurA, T288A, and D274N paralleled the behavior of these proteins in in vitro kinase assays performed in parallel to microinjections (FIG. 5C). Whereas aAurA was highly active and D274N was completely inactive, T288A became weakly active following brief incubation with cell lysates. Hence, the delayed resorption of cilia and ciliary shortening induced by T288A likely reflects the gradual emergence of an active pool of AurA following microinjection.

HDAC6 is Required for Ciliary Disassembly.

Little is known about the cellular machinery necessary for disassembling cilia. In seeking targets of AurA phosphorylation that might be relevant to this process, we considered the possibility that the acetylated α-tubulin commonly used to visualize cilia might play an active role in stabilizing the ciliary axoneme, based on reports that α-tubulin deacetylation promoted the in vivo destabilization of microtubules (Matsuyama et al., 2002). In particular, histone deacetylase 6 (HDAC6) has been identified as an important cytoplasmic tubulin deacetylase that influences mitosis and chemotaxis through regulating tubulin stability (Hubbert et al., 2002).

To assess whether altered regulation of tubulin acetylation might mediate HEF1/AurA signaling, we treated ciliated hTERT-RPE1 cells with small molecule deacetylase inhibitors, and established the ciliary disassembly profile (FIG. 7A). Both the broad-spectrum HDAC inhibitor trichostatin A (TSA), and tubacin, an inhibitor specifically targeting HDAC6 (Hideshima et al., 2005), completely blocked serum-induced ciliary disassembly, whereas niltubacin, an inactive analog of tubacin, and vehicle alone had no effect. Levels of acetylated tubulin were measured in treated cells, confirming that these were increased in cells treated with TSA and tubacin, but not in cells treated with niltubacin or control vehicle (FIG. 7B). As a control, because both AurA and HDAC inhibitors blocked ciliary disassembly, we considered the possibility that regulated ciliary disassembly might be generally sensitive to signaling inhibitors because of non-specific toxicities. However, serum induced disassembly with a normal profile in cells treated with inhibitors of GSK-3β and farnesyltransferase (FTI), indicating that blocked ciliary disassembly was specific response to impaired AurA and HDAC6 signaling (FIG. 7C).

To further confirm a specific requirement for HDAC6, we next established that cilia do not disassemble in serum-treated cells with siRNA-depleted HDAC6 (FIGS. 7D, 7E). Finally, we have microinjected aAurA into ciliated cells pre-treated for 3 hours with tubacin (FIG. 7F). Tubacin pre-treatment substantially limited the ability of microinjected AurA to disassemble cilia. Initial disassembly was slower, and in some cases transient, with a significant percentage of injected cells re-forming cilia by 1 hour after injection. As for AurA, neither tubacin treatment nor siRNA to HDAC6 influenced cell cycle profile at 2 h after serum stimulation, although both treatments led to accumulation in G2 at the later time point (FIGS. 8F, 8G). As a final control, we again used antibody to glutamylated tubulin as an independent means of scoring ciliary disassembly (FIG. 8E). The results of these experiments are equivalent to those obtained using antibody to acetylated α-tubulin (FIGS. 10A-C). Based on these data, we concluded that HDAC6 is an important downstream AurA effector for ciliary disassembly.

AurA Phosphorylates HDAC6 to Activate Tubulin Deacetylase Activity.

Taken together, our data suggested that the mechanism of ciliary disassembly by AurA requires intact HDAC6 deacetylation activity, to destabilize microtubules. AurA-dependent regulation of tubulin deacetylation may be direct or indirect. Importantly, although microinjection of AurA induced loss of ciliary α-acetylated tubulin as cilia disassemble, the non-ciliary α-acetylation of cytoplasmic microtubule networks were unaffected, suggesting a specific action of AurA and HDAC6 at the cilia (FIG. 10C). Further supporting this idea, HDAC6 localized to cilia in serum-starved cells and during the ciliary disassembly process (FIG. 9D and unpublished results), providing a ready target for AurA phosphorylation. Demonstrating a direct AurA-HDAC6 connection, antibody to AurA coimmunoprecipitated HDAC6 from hTERT-RPE1 cells (FIG. 9A). AurA-HDAC6 coimmunoprecipitation was not eliminated by pre-treatment of cells with PHA-680632, indicating that the association was not regulated by AurA activation status (FIG. 9A).

To directly determine whether HDAC6 might be an AurA substrate, recombinant activated AurA was used in an in vitro kinase assay with purified HDAC6, HDAC2, or GST, as in (Pugacheva and Golemis, 2005). AurA phosphorylated HDAC6, but not HDAC2 or the GST negative control (FIG. 9B). We next immunoprecipitated in vitro translated HDAC6 and a negative control, HDAC2, and gauged the relative ability of AurA to phosphorylate these proteins, and stimulate a tubulin deacetylase activity, in a defined in vitro assay. In reactions containing comparable levels of HDAC2 and HDAC6, only HDAC6 was phosphorylated by AurA (FIG. 9C). Moreover, AurA-phosphorylated HDAC6 was much more potent than unphosphorylated HDAC6 in deacetylating α-tubulin (FIG. 9C). These results lead us to conclude that AurA phosphorylation of HDAC6 stimulates HDAC6 deacetylase activity.

Ciliary Disassembly and Intraflagellar Transport (IFT).

Intraflagellar transport proteins perform important roles in mediating transport of proteins to and from the apical tip of cilia, and in many cases mutations in IFT proteins have been linked to ciliary dysfunction, loss of cilia, and pathological conditions (Sloboda, 2005). In contrast to depletion of HEF1 or AurA, depletion of representative IFT proteins IFT88 (FIGS. 6A-C) and IFT20 (FIG. 12) limits the initial formation of cilia in hTERT-RPE1 cells similar to reports in other cell types (Follit et al., 2006; Pazour et al., 2000). Based on immunofluorescence, cilia were only observed in IFT-depleted cells that retain at least some detectable IFT protein (FIG. 11C). This clear requirement of IFT proteins for ciliary assembly hinders the dissection of the contribution of these proteins in disassembly. However, intriguingly, the existing cilia in IFT88- or IFT20-depleted cells undergo minimal disassembly following serum stimulation, with the difference particularly noticeable at the early (2 h) timepoint (FIGS. 11C, 12). Further, depletion or inhibition of AurA alters the localization of IFT88 during the ciliary disassembly process. In untreated cells, IFT88 is seen intensely at the basal body and more diffusely along the axoneme of residual cilia two hours after serum stimulation, whereas in cells lacking active AurA, IFT88 accumulates at both the basal body and apical tip at this time point (FIG. 11D). It is likely that as in *Chlamydomonas* (Pan and Snell, 2005), IFT signaling mediates some aspects of ciliary disassembly.

Discussion

Cilia and flagella have been described as cellular "antennas", sensing a multiplicity of extracellular stimuli to induce an intracellular response (Singla and Reiter, 2006). In addition to undergoing regulated resorption induced by extracellular cues, for over four decades cilia have been known to be dynamically resorbed and resynthesized throughout the cell cycle. Taken in sum, our data suggest a model (FIG. 13) in which the serum growth factor-induced activation of a HEF1-AurA complex allows AurA to phosphorylate and activate HDAC6, which destabilizes the ciliary axoneme by deacetylating tubulin. Unexpectedly, activation of AurA is a central component of this cascade even during the G1 resorption wave, indicating a non-mitotic activity for AurA in animals.

An important finding of this work is the novel connection between AurA and HDAC6. HDAC6 tightly interacts with α and β tubulins through its HDAC domain, which may restrict its enzymatic activity, based on reports that taxol treatment causes HDAC6 to accumulate on microtubules, and is accompanied by increased tubulin acetylation (Zhang et al., 2003), Localized phosphorylation by AurA may increase the turnover of HDAC6 at microtubules, thus increasing the active pool of HDAC6 at cilia. Interestingly, studies in *Chlamydomonas* indicate that an important element of flagellar resorption is destabilization of the microtubule-based axoneme, suggesting this signaling cascade may be evolutionarily conserved (Pan and Snell, 2005; Pan et al., 2004). Further supporting the idea of conservation, the *C. elegans* gene MEC-12 encodes an α-tubulin variant that is specifically required only in mechanosensing neurons, which depend on intact cilia: MEC-12 is the only α-tubulin in this species with a conserved site for acetylation (Fukushige et al., 1999). Interestingly, HDAC6 has been reported to associate with protein phosphatase 1 (PP1) (Brash et al., 2004), which binds microtubules (Liao et al., 1998), and dephosphorylates and inactivates AurA kinase. Such feedback may limit AurA activation at cilia.

A number of growth stimuli induce HEF1 expression and phosphorylation, influencing its protein interactions. These include PDGF, which is here shown to partially induce ciliary disassembly (Natarajan et al., 2006). Intriguingly, recent studies of p130Cas, a protein structurally similar to HEF1, indicate that p130Cas acts as a stretch sensor; HEF1 contains all sequence motifs necessary for similar function (Kostic and Sheetz, 2006). As one major function of cilium is to sense fluid flow, and overly persistent flow has been reported to induce ciliary disassembly (Iomini et al., 2004), stretch sensation may be an important action of HEF1. Our data suggest that HEF1 both activates AurA and stabilizes the protein from degradation; it will be interesting to determine if the HEF1 scaffolding activity also contributes to AurA interaction with its effector HDAC6. Our data also indicate that AurA activity influences IFT88 localization during disassembly, and suggest integrity of the IFT system is important for the disassembly process in animals, as in *Chlamydomonas* (Pan and Snell, 2005).

Our establishment of a HEF1-AurA-HDAC6 cascade at cilia also informs the understanding of the mitotic activities of these proteins. Dynamic changes in microtubule acetylation and deacetylation characterize the stages of mitosis, and HDAC inhibitors that inhibit family members with microtubule deacetylase activity induce mitotic arrest (Blagosklonny et al., 2002). The identification here of HDAC6 as an AurA target suggests that HEF1-AurA regulation of tubulin deacetylation at mitosis through HDAC6 might offer a mechanism to fine-tune the mechanical properties of the mitotic spindle. This signaling cascade may also influence re-establishment of focal adhesions at and following cytokinesis, given the growing appreciation of the role of microtubules in guiding the formation of these structures (Ezratty et al., 2005; Strickland et al., 2005). Further, one intriguing possibility is that the common use of an AurA-HEF1-HDAC6 switch at the basal body of quiescent cells and the centrosome of G2/M cells may serve as part of a checkpoint mechanism coordinating responsiveness to extracellular cues at different points in cell cycle. In this context, our observation that inhibition of AurA causes appearance of mitotically arrested cells possessing both spindles and cilia (results not shown) may reflect triggering of such a centrosomally based checkpoint.

These results also have implications for the understanding and treatment of cancer. Tumor cells commonly do not have cilia, and both HEF1 and AurA are often upregulated in cancer. The roles for these proteins at the centrosome and focal adhesions described earlier already offer two mechanisms by which these proteins may promote tumor initiation and progression. The current study indicates a third mechanism, in which elevation of HEF1 or AurA in tumors may destabilize cilia, thus conditioning cellular response to external cues and impacting multiple signaling pathways. Further, AurA is regarded as a promising chemotherapeutic target, with agents inhibiting this protein currently in clinical trials (Andrews, 2005). TSA and other broad-spectrum agents targeting HDACs are used in the clinic (Vanhaecke et al., 2004), with more focused agents such as tubacin in preclinical development (Hideshima et al., 2005). Our data suggest that AurA- or HDAC-targeted drugs may have previously unappreciated in vivo effects involving cilia, that may contribute to the observed efficacy and/or side effects of these agents.

PKD is one of the best-described cilia-related diseases (Wilson, 2001), with mutation of the cilia-localized polycystin proteins 1 and 2 (PKD1 and PKD2) responsible for the significant majority of PKD patients, p130Cas interacts directly with complexes containing PKD1 and PKD2, and also with nephrocystins, cilia-associated proteins that are mutated in a second renal cystic syndrome, nephronophthisis (Benzing et al., 2001). Although an association of HEF1 with these proteins has never been assessed, HEF1 is abundant in the kidney and conserves many protein interaction sequences with p130Cas. It is also tantalizing to consider that closer connections exist between dysplastic disorders leading to cysts and cancer than have previously been appreciated. One of the surprising results of a recent large study to analyze the cancer genome was the identification of the PKHD1 protein, a ciliary protein which is mutant in autosomal recessive PKD, as commonly mutated in colorectal cancer (Sjoblom et al., 2006). Overall, deregulated AurA/HEF1/HDAC6 signaling may have broad implications for studies of human development and disease.

Example 2

Generation of a Mouse Model to Study PKD

At present, there are numerous competing models to explain the basis for cyst formation, and the differences between the various syndromes associated with kidney cysts. Studies of the signaling changes that occur in PKD have identified anomalous function of pathways that affect proliferation, cell cycle, and apoptosis (Edelstein, C. L. (2005) Cell Cycle 4:1550-4), Downstream elements of these signaling pathways include the tumor suppressors PTEN, TSC2, and p53, the oncogenes Bcl-2 and Akt, and other important growth regulators such as mTOR (Shillingford, J. M. et al. (2006) PNAS 103:5466-71). Current therapeutic strategies are attempting to exploit this information by using drags that target the relevant processes and pathways, such as the use of caspase inhibitors to reduce apoptosis, and mTOR inhibitors to block cell proliferation (Tao Y., et al. (2005) PNAS 102: 6954-9). In some cases, these approaches are alleviating symptoms and slowing cyst growth. However, no highly effective disease management strategy currently exists.

In the past several years, new insights into cyst pathogenesis have come from the consideration of the possible role of defects in renal cilia (Benzing et al., 2006; Snell, W. J., et al. Cell (2004) 117:693-7)). This "ciliary hypothesis" is based on the recognition that the protein products of genes mutated in PKD (and other pleiotropic syndromes involving cyst formation) both localize to cilia and impact ciliary function. Understanding the regulation of cilia in PKD, should provide the basis for novel therapeutic approaches to PKD.

In the past two years, increasing attention has focused on the identification of other structural and signaling proteins associated with the cilium, the basal body, or the adjacent plasma membrane. Importantly, many proteins that have been identified as the genetic cause of human developmental defects associated with polycystic kidney disease, including polycystins 1 and 2 (encoded by PKD1, PKD2), fibrocystin (PKHD1), nephrocystins (NPHP1, 3-5), and inversion (NPHP2), in each case localize to cilia. Additional disease-associated proteins localizing to cilia or basal bodies include the Bardet-Biedl Syndrome (BBS) proteins. Defects in BBS genes lead to kidney failure associated with renal cysts, and also loss of eyesight, obesity, and diabetes. Kartagener syndrome, characterized by reversed left-right symmetry ("situs inversus") of the heart, stomach and liver, as well as additional defects, arises from ciliary dyskinesia (Carlen B., et al., (2005) Ultrastruct. Pathol. (2005) 29:217-20). Finally, targeted or spontaneous mutation in mice of other cilia-associated proteins including the kinesin motor KIF3A or of Tg737/polaris, both involved in IFT, results in similar syndromes (Siroky, B. J., et al., (2006) Am J Physiol Renal Physiol.; Cano, D. A., et al., (2004) Development 131:3457-67; Yoder, B. K., et al., (2002) Am J Physiol Renal Physiol. 282:F541-52; Nishimura, T., et al., (2004) Nat Cell Biol. 6:328-34).

These and other studies make it clear that defects in proteins affecting ciliary functions are a major cause of renal cysts in general, and PKD in particular, as well as other serious diseases.

Mechanistically, the role of cilia in development and in disease is not yet well-defined, although the field is advancing rapidly (FIG. 14). Cilia protrude from the apical cells into adjacent lumenal space. In this space, extracellular flow of liquid bends the cilia in the direction away from the flow. This induces a mechanosensation signaling response, in which opening of a transient receptor potential (TRP) membrane-associated cation channel releases a pulse of $Ca^{2+}$ into cells. Polycystin 1 regulates the polycystin 2 TRP channel, and defects in these proteins (as well as other cilia-associated proteins) can cause defects in $Ca^{2+}$ uptake. This $Ca^{2+}$ signal propagates among neighboring renal cells within a tubule through gap junctions connecting the cells. Defects in other proteins such as Tg737/polaris cause additional defects involving IFT and signaling in cilia, in which the cilia are shortened; in mice defective for Tg737 (Oak Ridge Polycystic Kidney (orpk) mice), $Ca^{2+}$ increase is clearly abnormal (Siroky et al. (2006): Nishimura et al., (2004). Extending ciliary function, cilia are present and important for the growth of some cells not thought to be regulated by flow: in these cases, the cilia are thought to act as chemosensors, with signal transducing proteins accumulating at the basal body.

While many of the downstream signaling components activated by $Ca^{2+}$ are not yet well defined, the functional consequences of cilial bending for embryonic development are clearly profound. In development, cilial bending by extracellular fluid flow sends a polarity cue that conditions the future direction of cellular propagation. Inability to sense such flow is likely to underly the situs inversus observed in individuals mutant for some ciliary proteins such as inversion. In cell migration, fluid flow over cilia has been shown in some cases to contribute a polarity cue providing a direction for cell migration in development (Sawamoto K., et al. (2006) Science 311:629-32; Ciruna B., et al., (2006) Nature 439: 220-4). Within kidneys, flow sensing is thought to regulate proliferative response, such that defective sensing may cause overproliferation and cyst development. Separately, recently described connections between BBS proteins and the planar cell polarity (PCP) machinery imply that altered polarity of the cell division plane may cause dysplastic growth during maintenance of renal tubules, again leading to cyst formation (Fischer, E., et al., (2006) Nat Genet. 38:21-3; Ross, A. J., et al., (2005) Nat Genet. 37:1135-40).

An important point to consider is that as quiescent cells are induced to cycle, the cilium is reabsorbed, and the basal body returns to function within the centrosome, which includes action as microtubule organizing center (MTOC) for the bipolar spindle in mitosis. Although there are some differences among the cell systems used to study cell cycle regulation of cilia, most studies agree that cilia are reabsorbed by the time a cell enters mitosis, then re-form at several hours after the completion of cytokinesis (Quarmby et al., (2005). There are several implications of these findings. As discussed below, in addition to BBS, a number of other proteins have been identified at both basal bodies and centrosomes, and may act at both structures. These proteins may act directly at cilia and/or at centrosomes to orient the mitotic division plane of renal cells, allowing normal formation and maintenance of renal tubules. Conversely, as we demonstrate herein proteins that function at the centrosome to govern entry and exit from mitosis are ideally positioned to influence the formation and disassembly of cilia, and hence altered regulation of these proteins may contribute to the pathogenesis of PKD and related cilia-based syndromes.

Accordingly, the in vivo roles of AurA and HEF1 in cyst formation will be examined using mouse models. Appropriate models are available for this purpose. Notably, in late 2005, Seo et al. first described a HEF1 knockout mouse (Seo et al, (2005) J. Immunol. 175:3492-501). This knockout is viable and able to reproduce as a homozygote. To date, based on the interests of Sachiko Seo and her colleagues, characterization of these mice has been limited to the hematopoietic system. Even from this very limited analysis, it is clear that elimination of HEF1 has at least some phenotypic consequences, as B-cell maturation is defective. These mice will be utilized to explore the role of HEF1 in cell cycle and centrosome functions, and we have recently established a colony. Models for study of overexpressed AurA also exist (Fukuda et al., (2005) Mol. Cell Biol. 25:5270-81). However, in vivo overexpression of AurA has been reported as technically challenging, in part because of efficient proteasomal degradation of the protein. Further, AurA overexpression causes secondary phenotypes related to the failed cytokinesis seen in cells with too much AurA (Warner et al., (2003) Mol. Cancer Ther. 2:589-95). Instead, we will use small molecule inhibitors of AurA and HDACs to perform in vivo manipulation of these proteins.

Numerous mouse models have been developed for the study of PKD. Particularly because of the reported interaction of the HEF1-related protein p130Cas with polycystin, we wished to first explore the consequences of HEFT and AurA in modulation of PKD1-associated PKD. A particularly attractive model is the conditional floxed Pkd1 model developed by the Germino group (Piontek K. B., et al. (2004) J. Am. Soc. Nephol. 15:3035-43). Mating of these animals with mice expressing Cre recombinase causes somatic loss of Pkd1, and leads to formation of renal and hepatic cysts by 10 weeks of age.

Taken as a whole, our results clearly indicate that HEF1 and AurA are regulated in time and space in a manner compatible with a controlling role in ciliary disassembly. They also demonstrate that increased activity and/or expression of HEF1 and AurA actively promote ciliary disassembly, and that clinical agents that block AurA stabilize cilia. Importantly, these results validate genetic predictions from *Chlamydomonas* CALK, demonstrating evolutionary conservation of AurA regulation of cilia and flagella. This conservation allows us to exploit ongoing discoveries regarding CALK in *Chlamydomonas* to guide our future studies. In the context of these and other published works, we theorize that a basal body-associated complex including HEF1 and polycystin (and potentially other proteins) comprises a stretch- and growth factor-responsive sensor at the cilium. In normal cells, AurA localizes to the basal body, but is only activated following receipt of signals through the HEF1-containing stretch complex. We will analyze the factors contributing to AurA activation. We also hypothesize that upon activation, AurA phosphorylates substrates located in the basal body and cilia. We also expect to observe moderately elevated expression of wild type or even inactive AurA influences the activity of effectors regulating ciliary disassembly, as well as cilia-associated signaling proteins. Methods are also provided to elucidate the mechanisms by which AurA and HEF1 condition cilia-associated signaling responses, and promote ciliary disassembly. Finally, as mentioned above, the consequences of modulating HEF1, AurA, and HDAC6 upon cyst formation in a PKD mouse model system will also be assessed.

To generate the required mouse strains for the experiments, we will first take the HEF1$^{-/-}$ mice we have received from Seo and coworkers and backcrossed to a C57/Bl6 background. Our first step will be to create a series of mice that are heterozygous or homozygous null for HEF1 on a homozygous Pkd1$^{cond/cond}$ background. See Piontek et al. In parallel, we will cross the HEF1 null mice to the nestin$^{Cre}$ strain, ultimately creating mice heterozygous or homozygous null for HEF1, and hemizygously bearing the nestin$^{Cre}$ gene. Next, we will combine these strains of mice to allow us to examine the consequences of HEF1 status on cyst formation in Pkd1$^{cond/cond}$nestin$^{Cre}$ mice. These same mice can also be used for evaluation of the AurA and HDAC inhibitors. We emphasize, we do not view null status for HEF1 as independently likely to generate kidney cysts; rather, we expect the most likely activity will be to modify cyst formation induced by somatic mutation of Pkd1. See FIG. 15.

The central component of these experiments will be to compare rate and degree of cyst formation in HEF1$^{-/-}$Pkd1$^{cond/cond}$nestin$^{Cre}$, HEF1$^{wt/wt}$Pkd1$^{cond/cond}$nestin$^{Cre}$, and HEF1$^{-/-}$Pkd1$^{wt/wt}$nestin$^{Cre}$ mice. We anticipate that most HEF1$^{wt/wt}$Pkd1$^{cond/cond}$nestin$^{Cre}$ will have extensive cyst formation at 8-1.2 weeks of age. For each of the three strains of mice, we will sacrifice 10 animals at 8 and 16 weeks of age, and will use standard approaches to analyze timing, number, size, and pathological features of cyst formation. This will allow us to determine whether loss of HEF1 independently promotes cyst formation in the kidney, and whether lack of HEF1 positively or negatively regulates cyst formation dependent on defects in Pkd. We note, our crosses will also generate HEF1$^{-/wt}$Pkd1$^{cond/cond}$nestin$^{Cre}$ animals: if a significant effect is seen with HEF1 null status, we will then determine whether HEF1 heterozygous status has an intermediate phenotype.

We note that there is (at present) no evidence directly implicating mutation of HEF1, its family member p130Cas, or Aurora in hereditary PKD in humans. This may still emerge. However, we view it as more likely that mutation of these genes would have a broader effect: for instance, mice with loss of p130Cas are embryonic lethal. By contrast, elevated levels of p130Cas, AurA, and HEF1 (unpublished) are found in numerous cancers, and thought to promote deregulated cell growth. We believe similar conditioning of cell growth by some of these proteins occurs in PKD. The methods disclosed herein will lead to the creation of new therapeutic strategies to treat PKD, by providing the scientific basis to apply existing compounds already in use for treatment of cancer to this disease. Moreover, the mice described herein will provide an in vivo model to assess the efficacy of various agents that may be useful for the treatment of diseases associated with aberrant cilia formation, such as PKD In addition, by improving our understanding of the molecular basis of PKD, we may be able to better predict disease progression and severity. Overall, the goal is to reduce the incidence and/or severity of PKD in those genetically prone to the disease, alleviate the symptoms of PKD in early stage patients, and limit the number of PKD patients that progress to end stage renal failure.

REFERENCES

Anand, S., Penrhyn-Lowe, S., and Venkitaraman, A. R. (2003). AURORA-A amplification overrides the mitotic spindle assembly checkpoint, inducing resistance to Taxol. Cancer Cell 3, 51-62.

Andrews, P. D. (2005). Aurora kinases: shining lights on the therapeutic horizon?Oncogene 24, 5005-5015.

Benzing, T., Gerke, P., Hopker, K., Hildebrandt, F., Kim, E., and Walz, G. (2001). Nephrocystin interacts with Pyk2, p130(Cas), and tensin and triggers phosphorylation of Pyk2. Proc Natl Acad Sci USA 98, 9784-9789.

Benzing, T., and Walz, G. (2006). Cilium-generated signaling: a cellular GPS? Curr Opin Nephrol Hypertens 15, 245-249.

Bischoff, J. R., Anderson, L., Zhu, Y., Mossie, K., Ng, L., Souza, B., Schryver, B., Flanagan, P., Clairvoyant F., Ginther, C, et al., (1998). A homologue of Drosophila aurora kinase is oncogenic and amplified in human colorectal cancers. Embo J 17, 3052-3065.

Blagosklonny, M. V., Robey, R., Sackett, D. L., Du, L., Traganos, F., Darzynkiewicz, Z., Fojo, T., and Bates, S. E. (2002). Histone deacetylase inhibitors all induce p21 but differentially cause tubulin acetylation, mitotic arrest, and cytotoxicity. Mol Cancer Ther 1, 937-941.

Bradley, B. A., and Quarmby, L. M. (2005). A NIMA-related kinase, Cnk2p, regulates both flagellar length and cell size in *Chlamydomonas*. J Cell Sci 118, 3317-3326.

Brush, M. H., Guardiola, A., Connor, J. H., Yao, T. P., and Shenolikar, S. (2004). Deactylase inhibitors disrupt cellular complexes containing protein phosphatases and deacetylases. J Biol Chem 279, 7685-7691.

Cano, D. A., Murcia, N, 8., Pazour, G. J., and Hebrok, M. (2004). Orpk mouse model of polycystic kidney disease reveals essential role of primary cilia in pancreatic tissue organization. Development 131, 3457-3467.

Ezratty, E, J., Partridge, M. A., and Gundersen, G. G. (2005). Microtubule-induced focal adhesion disassembly is mediated by dynamin and focal adhesion kinase. Nat Cell Biol 7, 581-590.

Follit, J. A., Tuft, R. A., Fogarty, K. E., and Pazour, G. J. (2006). The intraflagellar transport protein IFT20 is associated with the Golgi complex and is required for cilia assembly. Mol Biol Cell 17, 3781-3792.

Fukushige, T., Siddiqui, Z. K., Chou, M., Culotti, J. G., Gogonea, C. B., Siddiqui, S. S., and Hamelin, M. (1999). MEC-12, an alpha-tubulin required for touch sensitivity in C, elegans. J Cell Sci 112 (Pt 3), 395-403.

Goepfert, T. M., Adigun, Y. E., Zhong, L., Gay, J., Medina, D., and Brinkley, W. R. (2002). Centrosome amplification and overexpression of aurora A are early events in rat mammary carcinogenesis. Cancer Res 62, 4115-4122.

Gritsko, T. M., Coppola, D., Paciga, J. E., Yang, L., Sun, M., Shelley, S. A., Fiorica, J. V., Nicosia, S. V., and Cheng, J. Q. (2003). Activation and overexpression of centrosome kinase BTAK/Aurora-A in human ovarian cancer. Clin Cancer Res 9, 1420-1426.

Hideshima, T., Bradner, J. E., Wong, J., Chauhan, D., Richardson, P., Schreiber, S. L., and Anderson, K. C. (2005). Small-molecule inhibition of proteasome and aggresome function induces synergistic antitumor activity in multiple myeloma. Proc Natl Acad Sci USA 102, 8567-8572.

Huangfu, D., and Anderson, K. V. (2005). Cilia and Hedgehog responsiveness in the mouse. Proc Natl Acad Sci USA 102, 11325-11330.

Hubbert, C, Guardiola, A., Shao, R., Kawaguchi, Y., Ito, A., Nixon, A., Yoshida, M., Wang, X. F., and Yao, T. P. (2002). HDAC6 is a microtubule-associated deacetylase. Nature 417, 455-458.

Iomini, C, Tejada, K., Mo, W., Vaananen. H., and Piperno, G. (2004). Primary cilia of human endothelial cells disassemble under laminar shear stress. J Cell Biol 164, 811-817.

Kim, M., Gans, J. D., Nogueira, C, Wang, A., Paik, J. H., Feng, B., Brennan, C, Hahn, W. C, Cordon-Cardo, C, Wagner, S. N., et al. (2006). Comparative oncogenomics identifies NEDD9 as a melanoma metastasis gene. Cell 125, 1269-1281.

Kostic, A., and Sheetz, M. P. (2006). Fibronectin Rigidity Response through Fyn and p130Cas Recruitment to the Leading Edge. Mol Biol Cell.

Law, S. F., Estojak, J., Wang, B., Mysliwiec, T., Kruh, G. D., and Golemis, E. A. (1996). Human Enhancer of Filamentation 1 (HEF1), a novel p130Cas-like docking protein, associates with FAK, and induces pseudohyphal growth in yeast. Mol Cell Biol 16, 3327-3337.

Law, S. F., Zhang, Y.-Z., Klein-Szanto, A., and Golemis, E. A. (1998). Cell-cycle regulated processing of HEF1 to multiple protein forms differentially targeted to multiple compartments. Mol Cell Biol 18, 3540-3551.

Liao, H., Li, Y., Brautigan, D. L., and Gundersen, G. G. (1998). Protein phosphatase 1 is targeted to microtubules by the microtubule-associated protein Tau. J Biol Chem 273, 21901-21908.

Liu, A., Wang, B., and Niswander, L. A. (2005). Mouse intraflagellar transport proteins regulate both the activator and repressor functions of Gli transcription factors. Development 132, 3103-3111.

Marshall, W. F., Qin, H., Rodrigo Brenni, M., and Rosenbaum, J. L. (2005). Flagellar length control system: testing a simple model based on intraflagellar transport and turnover, Mol Biol Cell 16, 270-278.

Marumoto, T., Zhang, D., and Saya, H. (2005). Aurora-A—a guardian of poles, Nat Rev Cancer J, 42-50.

Matsuyama, A., Shimazu, T., Sumida, Y., Saito, A., Yoshimatsu, Y., Seigneurin-Berny, D., Osada, H., Komatsu, Y., Nishino, N., Khochbin, S., et al. (2002). In vivo destabilization of dynamic microtubules by HDAC6-mediated deacetylation. Embo J 27, 6820-6831.

Minn, A. J., Gupta, G. P., Siegel, P. M., Bos, P. D., Shu, W., Giri, D. D., Viale, A., Olshen, A. B., Gerald, W. L., and Massague, J. (2005). Genes that mediate breast cancer metastasis to lung. Nature 436, 518-524.

Natarajan, M., Stewart, J. E., Golemis, E. A., Pugacheva, E. N., Alexandropoulos, K., Cox, B. D., Wang, W., Grammer, J. R., and Gladson, C. L. (2006). HEF1 is a necessary and specific downstream effector of FAK that promotes the migration of glioblastoma cells. Oncogene 25, 1721-1732.

O'Neill, G. M., Fashena, S. J., and Golemis, E. A. (2000). Integrin signaling: a new Cas(t) of characters enters the stage. Trends Cell Biol 10, 111-119.

Pan, J., and Snell, W. J. (2005). *Chlamydomonas* shortens its flagella by activating axonemal disassembly, stimulating IFT particle trafficking, and blocking anterograde cargo loading. Dev Cell 9, 431-438.

Pan, J., Wang, Q., and Snell, W T. J. (2004). An aurora kinase is essential for flagellar disassembly in *Chlamydomonas*. Dev Cell 6, 445-451.

Pan, J., Wang, Q., and Snell, W. J. (2005). Cilium-generated signaling and cilia-related disorders. Lab Invest 85, 452-463.

Pazour, G. J., Dickert, B. L., Vucica, Y., Seeley, E. S., Rosenbaum, J. L., Witman, G. B., and Cole, D. G. (2000). *Chlamydomonas* IFT88 and its mouse homologue, polycystic kidney disease gene tg737, are required for assembly of cilia and flagella. J Cell Biol 151, 709-718.

Pugacheva, E. N., and Golemis, E. A. (2005). The focal adhesion scaffolding protein HEF1 regulates activation of the Aurora-A and Nek2 kinases at the centrosome. Nat Cell Biol 7, 937-946.

Pugacheva, E. N., and Golemis, E. A. (2006). HEF1-aurora A interactions: points of dialog between the cell cycle and cell attachment signaling networks. Cell Cycle 5, 384-391.

Quarmby, L. M. (2004). Cellular deflagellation. Int Rev Cytol 233, 47-91.

Quarmby, L. M., and Parker, J. D. (2005), Cilia and the cell? cycle J Cell Biol 169, 707-710.

Rieder, C. L., Jensen, C. G., and Jensen, L. C. (1979). The resorption of primary cilia during mitosis in a vertebrate (PtK1) cell line. J Ultrastruct Res 68, 173-185.

Satinover, D. L., Leach, C. A., Stukenberg, P. T., and Brautigan, D. L. (2004). Activation of Aurora-A kinase by protein phosphatase inhibitor-2, a bifunctional signaling protein. Proc Natl Acad Sci USA 101, 8625-8630.

Schneider, L., Clement, C. A., Teilmann, S. C, Pazour, G. J., Hoffmann, E, K., Satir, P., and Christensen, S. T. (2005). PDGFRalphaalpha signaling is regulated through the primary cilium in fibroblasts. Curr Biol 15, 1861-1866.

Simons, M., Gloy, J., Ganner, A., Bullerkotte, A., Bashkurov, M., Kronig, C., Schermer, B., Benzing, T., Cabello, O. A., Jenny, A., et al. (2005). Inversion, the gene product mutated in nephronophthisis type II, functions as a molecular switch between Wnt signaling pathways. Nat Genet 37, 537-543.

Singla, V., and Reiter, J. F. (2006). The primary cilium as the cell's antenna: signaling at a sensory organelle. Science 313, 629-633.

Sjoblom, T., Jones, S., Wood, L. D., Parsons, D. W., Lin, J., Barber, T., Mandelker, D., Leary, R. J., Ptak, J., Silliman, N et al. (2006), The Consensus Coding Sequences of Human Breast and Colorectal Cancers. Science.

Sloboda, R. D. (2005). Intraflagellar transport and the flagellar tip complex. J Cell Biochem 94, 266-272.

Soncini, C, Carpinelli, P., Gianellini, L., Fancelli, D., Vianello, P., Rusconi, L., Storici, P., Zugnoni, P., Pesenti, E, Croci, V., et al. (2006). PHA-680632, a novel Aurora kinase inhibitor with potent antitumoral activity, Clin Cancer Res 12, 4080-4089.

Strickland, L. L, Wen, Y., Gundersen, G. G., and Burgess, D. R. (2005). Interaction between EB1 and p150glued is required for anaphase astral microtubule elongation and stimulation of cytokinesis. Curr Biol 15, 2249-2255.

Tanaka, Y., Okada, Y., and Hirokawa, N. (2005). FGF-induced vesicular release of Sonic hedgehog and retinoic acid in leftward nodal flow is critical for left-right determination. Nature 435, 172-177.

Tucker, R. W., Pardee, A. B., and Fujiwara, K. (1979). Centriole dilation is related to quiescence and DNA synthesis in 3T3 cells. Cell 17, 527-535.

Vanhaecke, T., Papeleu, P., Elaut, G., and Rogiers, V, (2004). Trichostatin A-like hydroxamate histone deacetylase inhibitors as therapeutic agents: toxicological point of view. Curr Med Chem 11, 1629-1643.

Wilson, P. D. (2001). Polycystin: new aspects of structure, function, and regulation. J Am Soc Nephrol 12, 834-845.

Zhang, Y., Li, N., Caron, Cowith and deacetylates tubulin and microtubules in vivo. Embo J 22, 1168-1179.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method for identifying agents which modulate ciliary function and assembly/disassembly comprising:
   a) providing cells which express AurA, HDAC6 and HEF1;
   b) incubating said cells in the presence and absence of a test agent; and
   c) assessing activation of HDAC6 and resorption of cilia present on said cells;

wherein an alteration in resorption of cilia or HDAC6 activation in the presence but not the absence of said agent, is indicative of agents which modulate ciliary function and assembly/disassembly.

2. The method of claim 1 wherein the resorption of cilia of step c) is assessed via immunohistochemistry, immunocytochemistry, live cell imaging and/or electron microscopy.

3. The method of claim 1, wherein said cells are selected from the group consisting of canine kidney polarized epithelial cells (MDCK), mouse kidney collecting duct tubule cells (IMCD3), human renal cells (Caki-1), and human retinal pigmented epithelial cells (HTERT-RPE-1).

4. The method of claim 2, wherein integrity of cilia is assessed via localization of $\alpha$-tubulin and $\gamma$-tubulin.

5. The method of claim 1 wherein said agent is selected from the group consisting of siRNA, HDAC inhibitors, and small molecule inhibitors of Aurora A kinase.

6. The method of claim 1 wherein said agent promotes ciliary disassembly.

7. The method of claim 1, wherein said agent inhibits ciliary disassembly.

8. The method of claim 1, wherein said agent alters a characteristic selected from the group consisting of HDAC6 phosphorylation, HDAC6 deacetylase activity, HDAC6 localization to cilia and length, number and stability of cilia.

* * * * *

UNITED STATES PATENT AND TRADEMARK OFFICE
CERTIFICATE OF CORRECTION

PATENT NO.       : 8,685,658 B2                                    Page 1 of 1
APPLICATION NO.  : 12/374209
DATED            : April 1, 2014
INVENTOR(S)      : Golemis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 641 days.

Signed and Sealed this

Twenty-ninth Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,685,658 B2
APPLICATION NO. : 12/374209
DATED : April 1, 2014
INVENTOR(S) : Erica A. Golemis and Elena N. Pugacheva It is certified that error appears in the above-identified patent and that said Letters Patent is hereby corrected as shown below:

In the Specification

Column 1, Lines 12-16, delete the paragraph:
"Pursuant to 35 U.S.C. §202(c), it is acknowledged that the U.S. Government has certain rights in the invention described, which was made in part with funds from the National Institutes of Health, Grant Numbers RO1 CA63366 and CA-06927."
And insert therefor:
--This invention was made with government support under CA063366 and CA006927 awarded by the National Institutes of Health. The government has certain rights in the invention.--

Signed and Sealed this
Twenty-second Day of August, 2023

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: siRNA oligonucleotide sense strand

<400> SEQUENCE: 1
gguauaucag gugccaccat t                                         21

<210> SEQ ID NO 2
<211> LENGTH: 23
<212> TYPE: DNA
<213> ORGANISM: Artificial Sequence
<220> FEATURE:
<223> OTHER INFORMATION: siRNA oligonucleotide sense strand

<400> SEQUENCE: 2 aaggggbuaua ugccauuccg ctt                                      23
```